United States Patent
Schlechtingen et al.

(10) Patent No.: US 9,751,834 B2
(45) Date of Patent: Sep. 5, 2017

(54) OXYGENATED AMINO- OR AMMONIUM-CONTAINING SULFONIC ACID, PHOSPHONIC ACID AND CARBOXYLIC ACID DERIVATIVES AND THEIR MEDICAL USE

(75) Inventors: Georg Schlechtingen, Cologne (DE); Hans-Joachim Knölker, Dresden (DE); Tim Friedrichson, Dresden (DE); Gary Jennings, Dresden (DE); Tobias Braxmeier, Kuppenheim (DE)

(73) Assignee: GRI BIO, INC., San Diego, CA (US)

( * ) Notice: Subject to any disclaimer, the term of this patent is extended or adjusted under 35 U.S.C. 154(b) by 547 days.

(21) Appl. No.: 14/403,168

(22) PCT Filed: May 25, 2012

(86) PCT No.: PCT/EP2012/059810
§ 371 (c)(1),
(2), (4) Date: Apr. 23, 2015

(87) PCT Pub. No.: WO2012/160186
PCT Pub. Date: Nov. 29, 2012

(65) Prior Publication Data
US 2015/0284320 A1   Oct. 8, 2015

(30) Foreign Application Priority Data
May 26, 2011   (EP) .................................... 11167731

(51) Int. Cl.
C07C 309/14   (2006.01)
A61K 31/205   (2006.01)

(52) U.S. Cl.
CPC .......... C07C 309/14 (2013.01); A61K 31/205 (2013.01)

(58) Field of Classification Search
CPC ............................ C07C 309/14; A61K 31/205
See application file for complete search history.

(56) References Cited

U.S. PATENT DOCUMENTS

| | | |
|---|---|---|
| 3,280,179 A | 10/1966 | Ernst |
| 3,432,408 A | 3/1969 | Brown et al. |
| 4,085,134 A | 4/1978 | Redmore et al. |
| 5,545,667 A | 8/1996 | Wiersema et al. |
| 6,004,771 A | 12/1999 | Thornton |
| 6,136,857 A | 10/2000 | Wiersema et al. |
| 6,406,880 B1 * | 6/2002 | Thornton ................ C12Q 1/18 435/253.1 |
| 2003/0185816 A1 | 10/2003 | Olesen |
| 2015/0232418 A1 | 8/2015 | Schlechtingen et al. |
| 2016/0016981 A1 | 1/2016 | Schlechtingen et al. |

FOREIGN PATENT DOCUMENTS

| | | |
|---|---|---|
| CA | 2886676 A1 | 11/2012 |
| CA | 2886683 A1 | 11/2012 |
| CA | 2887385 A1 | 11/2012 |
| CN | 101456810 A | 6/2009 |
| EP | 0569028 A2 | 11/1993 |
| EP | 2 739 606 A1 | 6/2014 |
| EP | 2 809 318 A1 | 12/2014 |
| EP | 2 809 648 A1 | 12/2014 |
| FR | 1326561 A | 5/1963 |
| HK | 1198160 A | 3/2015 |
| HK | 1204554 A | 11/2015 |
| HK | 1204602 A | 11/2015 |
| JP | 2010-120998 A | 6/2010 |
| WO | WO 2005/000288 A2 | 1/2005 |
| WO | WO 2007/071402 A1 | 6/2007 |
| WO | WO 2009/136396 A2 | 11/2009 |
| WO | WO 2010/055028 A2 | 5/2010 |
| WO | WO 2012/160186 A1 | 11/2012 |
| WO | WO 2012/160187 A1 | 11/2012 |
| WO | WO 2012/160188 A1 | 11/2012 |

OTHER PUBLICATIONS

L. Yan et al. "Design and synthesis of conformationally constrained 3-(N-alkylamino)propylphosphonic acids as potent agonists of sphingosine-1-phosphate (S1P) receptors" Bioorganic & Medicinal Chemistry Letters, Aug. 20, 2004, p. 4861-4866, vol. 14.

N. Parris et al. "Soap Based Detergent Formulations, V. Amphoteric Lime Soap Dispersing Agents" Journal of the American Oil Chemists' Society, Dec. 1973, p. 509-511 vol. 50.

Laurent Germanaud et al. "Summaries of neutral amphiphiles phosphobetaines to intercharge varying distances" Bulletin de la Sociètè Chimique de France, Jan.-Feb. 1988, p. 699-704.

C.R. Birnie et al. "Antimicrobial Evaluation of N-Alkyl Betaines and N-Alkyl-N, N-Dimethylamine Oxides with Variations in Chain Length" Antimicrobial Agents and Chemotherapy. Sep. 2000, p. 2514-2517. vol. 44. No. 9.

M.P. Hudock et al. "Inhibition of Geranylgeranyl Diphosphate Synthase by Bisphosphonates: A Crystallographic and Computational Investigation"Journal of Medical Chemistry 2008, p. 5594-5607. vol. 51. No. 18.

(Continued)

*Primary Examiner* — Sudhakar Katakam
(74) *Attorney, Agent, or Firm* — Knobbe Martens Olson & Bear LLP

(57) ABSTRACT

The present invention relates to oxygenated amino or ammonium-containing sulfonic acid, phosphonic acid and carboxylic acid derivatives, in particular the compounds of formula 1, 2, 3, 4, 5 or 6, and their medical use, including their use in the treatment, prevention or amelioration of an inflammatory, autoimmune and/or allergic disorder, or a proliferative, neoplastic or dysplastic disease or disorder.

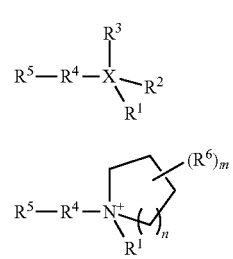

2 Claims, 12 Drawing Sheets

(56) References Cited

OTHER PUBLICATIONS

Figure 1:
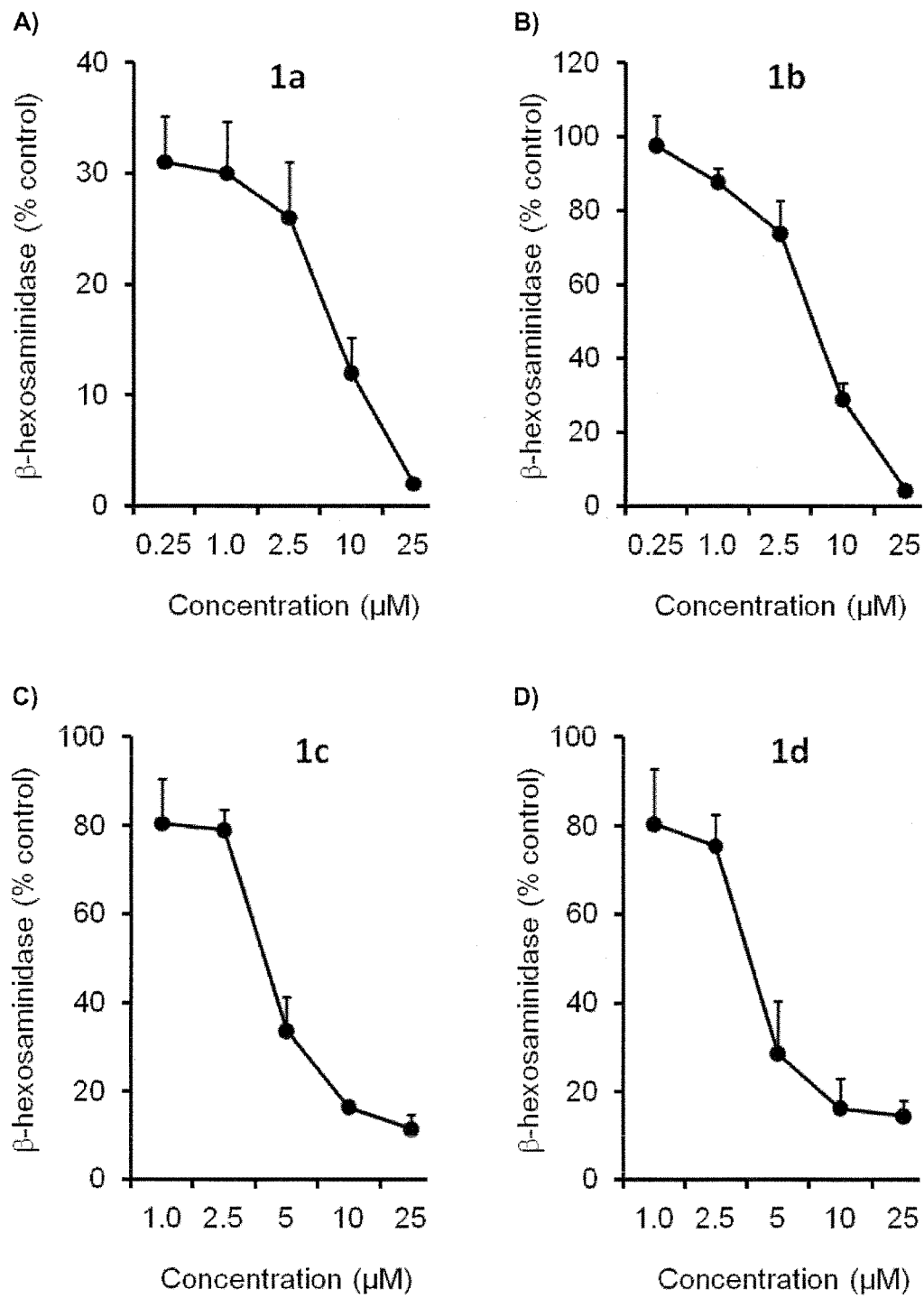
Figure 1:
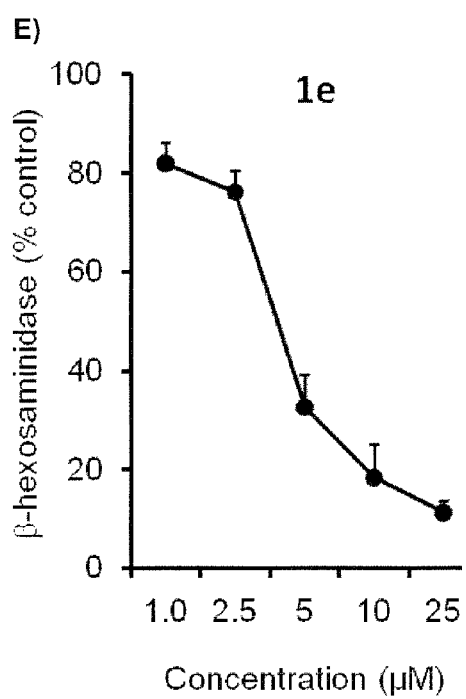
Figure 1:
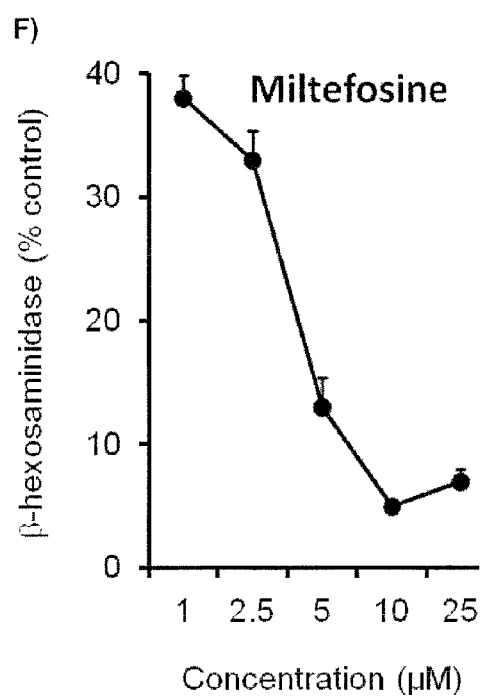

F. Y. Rachinkskii et al. "N-Alkyl-N-Alkarboxymethylhexamethylenimmonium Derivatives"(Communication II of a series of works on the synthesis and investigation of hexamethylenimmonium compounds as bactericides) Zhurnal Prikladnoi Khimii, October 1968, p. 2326-2329. vol. 41. No. 10.
Database Registry. Chemical Abstracts Service. RN 23035-15-6. Nov. 16, 1984.
Database Registry. Chemical Abstracts Service. RN 761356-67-6. Oct. 12, 2004.
International Search Report dated Oct. 1, 2012 for co-pending PCT Application No. PCT/EP2012/059810.
International Search Report dated Oct. 1, 2012 for related PCT Application No. PCT/EP2012/059812.
International Search Report dated Sep. 26, 2012 for related PCT Application No. PCT/EP2012/059813.
Database CAPLUS in STN, Acc. No. 1967:30267, Ernst, U.S. Pat. No. 3,280,179 A (Oct. 18, 1966) (abstract).
Office Action received in Canadian Application No. 2,886,676, dated Sep. 23, 2015, in 3 pages.
Communication Pursuant to Rules 161(1) and 162 EPC in EP Application No. 12730164.6, dated Feb. 5, 2015 in 2 pages.
International Preliminary Report on Patentability and Written Opinion received in PCT Application No. PCT/EP2012/059810, dated Dec. 5, 2013 in 10 pages.
Office Action received in Canadian Application No. 2,886,683, dated Sep. 22, 2015, in 7 pages.
International Preliminary Report on Patentability and Written Opinion received in PCT Application No. PCT/EP2012/059812, dated Dec. 5, 2013 in 11 pages.
Office Action received in Canadian Application No. 2,887,385, dated Sep. 8, 2015, in 3 pages.
International Preliminary Report on Patentability and Written Opinion received in PCT Application No. PCT/EP2012/059813, dated Dec. 5, 2013 in 8 pages.
Office Action dated Mar. 21, 2017, issued in corresponding CA Application No. 2,886,676.
Office Action dated Mar. 23, 2017, issued in related U.S. Appl. No. 14/403,167.
Database CAPLUS in STN, Acc. No. 2001:935430, Olesen et al., US 2003/0185816 A1 (part of patent family Wo 2001//097837)(Oct. 2, 2003)(abstract).

\* cited by examiner

A)

Days after collagen type II administration c)

OXYGENATED AMINO- OR AMMONIUM-CONTAINING SULFONIC ACID, PHOSPHONIC ACID AND CARBOXYLIC ACID DERIVATIVES AND THEIR MEDICAL USE

The present invention relates to oxygenated amino or ammonium-containing sulfonic acid, phosphonic acid and carboxylic acid derivatives, in particular the compounds of formula 1, 2, 3, 4, 5 or 6, and their medical use, including their use in the treatment, prevention or amelioration of an inflammatory, autoimmune and/or allergic disorder, or a proliferative, neoplastic or dysplastic disease or disorder.

Without being bound by theory, the compounds provided herein are considered to exert their pharmacological activity through inhibition of the phosphoinositide 3-kinase (PI3K)/Akt kinase pathway. The serine/threonine protein kinase Akt (also known as Protein Kinase B) is a key mediator of signal transduction. Akt is activated by numerous receptors, including those of growth factors, cytokines, hormones and insulin as well as by the attachment of cells to the extracellular matrix. Once activated, the plasma membrane receptors stimulate the activity of PI3K to generate phosphatidylinositol-3,4,5-trisphosphate (PIP3), a lipid second messenger essential for the translocation of Akt, which contains a PIP3-binding pleckstrin homology (PH)-domain, from the cytoplasm to the plasma membrane (Franke et al., Cell 81:727-736, (1995)). Once recruited to the membrane, it is phosphorylated and activated by other kinases (Hemmings, Science 275:628-630 (1997); Hemmings, Science 276:534 (1997); Downward, Science 279:673-674 (1998); Alessi et al., EMBO J. 15:6541-6551 (1996)), such as PDK1 and mTORC2.

Akt in turn is responsible for regulating the function of many cellular proteins involved in processes such as transcription, cell proliferation and apoptosis (programmed cell death), angiogenesis, cell motility and glucose metabolism (Kulik et al., Mol Cell Biol. 17:1595-1606 (1997); Franke et al., Cell 88:435-437 (1997); Kaufmann-Zeh et al., Nature 385:544-548 (1997); Hemmings, Science 275:628-630 (1997); Dudek et al., Science 275:661-665 (1997)). Activated PI3K/Akt pathway protects cells from apoptosis and by acting as a modulator of anti-apoptotic signalling in tumor cells, Akt is a target for cancer therapy. Blocking the PI3K/Akt pathway could therefore simultaneously inhibit the proliferation of tumor cells and sensitize towards pro-apoptotic agents (Falasca, Curr Pharm Des. 16:1410-6 (2010)).

These findings indicate that Akt may be a drug target for the treatment of inflammation, autoimmune diseases and allergy as well as cancer. Accordingly, the compounds provided herein, in particular the compounds of formula 1, 2, 3, 4, 5 or 6, are useful in the treatment, prevention or amelioration of such illnesses.

Broad-acting immunomodulatory drugs such as corticosteroids, calcineurin inhibitors and cyclosporin are highly effective and have been used for the therapy of allergic and cellular inflammatory diseases, including autoimmune diseases, for many years. They are potent in suppressing both Th1 and Th2 driven processes, yet they suffer from undesirable side-effects, which limit their therapeutic window. Corticosteroids regulate the expression of numerous genes and, consequently, their use is limited by severe adverse effects. Typical serious adverse effects of short-term corticosteroids use are disturbances in water and salt retention, lipid metabolism, skin thinning and changes in behaviour. More serious adverse effects associated with long-term systemic exposure to corticosteroids include increased appetite and weight gain, deposits of fat in chest, face, upper back, and stomach, water and salt retention leading to swelling and edema, high blood pressure, diabetes, slowed healing of wounds, osteoporosis, cataracts, acne, muscle weakness, thinning of the skin, increased susceptibility to infection, stomach ulcers, increased sweating, mood swings, psychological problems such as depression, adrenal suppression and crisis.

More specifically targeted therapeutics, such as biologics, e.g., antibodies against certain cytokines or their receptors, inhibit a single protein target and are effective in certain situations, but only address one of the targets in a highly redundant inflammatory cascade and are hence often used in combination therapy, as effective resolution of inflammatory diseases requires several targets to be addressed simultaneously.

There is a high unmet medical need for new drugs that curb the underlying disease processes. For instance, in rheumatoid arthritis (RA) such disease-modifying antirheumatic drugs (DMARDs) can slow down progressive joint destruction reducing long-term disease severity. This provides both therapeutic and economic advantages by shortening the therapeutic period and reducing the dose of concomitant medications.

Many chronic inflammatory diseases, including autoimmune diseases such as rheumatoid arthritis (RA), are associated with deregulated intracellular signal transduction pathways, including the phosphoinositide 3-kinase (PI3K)/Akt kinase pathway, and the resultant pathogenic interactions between immune and connective tissue stromal cells lead to changes in cell activation, proliferation, migratory capacity, and cell survival that contribute to inflammation (Tas et al., Curr Pharm Des. 11:581-611 (2005)). For example, abnormal functioning, differentiation and/or activation of T-cells, B-cells and myeloid cells have been documented in various autoimmune diseases, including rheumatoid arthritis (RA), diabetes mellitus, lupus and multiple sclerosis and studies have detailed anomalous activation of the Akt signalling axis in the context of systemic autoimmunity (Wu et al., Disord Drug Targets. 9:145-50 (2009)).

Akt is an important signal transduction pathway mediating the delay of neutrophil apoptosis by inflammatory mediators, during neutrophil activation, during inflammation (Rane and Klein, Front Biosci. 14:2400-12 (2009)) and control over neutrophil and macrophage migration and apoptosis is a key factor in the pathogenesis of the majority of chronic inflammatory diseases.

RA is a chronic inflammatory disease, which results in inflammation of the synovial lining and destruction of the adjacent bone and cartilage. Synovial macrophages, fibroblasts and lymphocytes are critical to the pathogenesis of this disease, in which apoptosis plays divergent roles. Signaling pathways, such as PI3K/Akt, are highly activated in the RA joint, contributing to the expression of aenes that cause inflammation and destruction and expression of a variety of anti-apoptotic molecules. Induction of apoptosis of macrophages, synovial fibroblasts or lymphocytes, through inhibition of the expression of anti-apoptotic molecules, could be therapeutically beneficial in RA (Liu and Pope, Curr Opin Pharmacol. 3:317-22 (2003)). Furthermore, results suggest that signal transduction pathways dependent on PI3K/Akt are involved in the overproduction of the key inflammatory cytokine IL-17 in patients with rheumatoid arthritis (Kim et al., Arthritis Res Ther. 7:R139-148 (2005)).

Akt is closely associated with key membrane-bound receptors and represents a convergent integration point for multiple stimuli implicated in COPD pathogenesis. Akt is also implicated in the systemic manifestations of COPD such as skeletal muscle wasting and metabolic disturbances. As such, Akt represents a particularly attractive therapeutic target for the treatment of COPD (Bozinovski et al., Int J Chron Obstruct Pulmon Dis. 1:31-38 (2006)).

The compounds provided herein are positioned to be disease-modifying drugs. The compounds have potential for application in a wide variety of chronic inflammatory indications and in combination with a favorable tolerability, the products can be expected to gain adoption by a significant number of patients suffering from the severe side effects of current treatments. Furthermore, the compounds provided herein will be suitable not only for monotherapy but also in combination with existing therapies, which address specific disease targets but are not sufficient to resolve the disease alone.

WO 2007/071402 describes the use of certain inner ionic phospholipids, phosphonolipids and phosphate derivatives for the treatment or prevention of allergic diseases.

Furthermore, specific quaternary ammonium compounds are disclosed in U.S. Pat. No. 5,545,667 and U.S. Pat. No. 6,136,857 to be useful as antineoplastic agents. These compounds comprise a specific unsubstituted alkylene group connecting a terminal acid group to the quaternary nitrogen atom and are thus different from the compounds of the invention which comprise, inter alia, an alkylene ($R^4$) substituted with an oxygen-containing group. Coy E A et al. *Int J Immunopharmacol.* 1990; 12(8):871-81 report a generalized antiproliferative activity of specific amphiphilic molecules on T-lymphocytes and on a variety of tumor cell lines and a lack of specificity for the immune system. WO 2009/136396 relates to certain sulfobetaines to be used in the treatment of cancer, obesity, age-related macular degeneration and neurodegenerative diseases. WO 92/16201 relates to the use of specific betaine compounds for the treatment of certain viral infections. Yan L, et al. *Bioorg Med Chem Lett.* 2004; 14(19):4861-6 describe certain aminopropyl-phosphonic acid derivatives as agonists of sphingosine-1-phosphate G protein-coupled receptors. In WO 2005/000288, specific aminoalkyl-sulfonic acid compounds are disclosed for the treatment of protein Aggregation disorders. Further specific quaternary ammonium compounds are, for example, disclosed in: Ernst R et al. *Toxicology.* 1980; 15(3):233-42; Speijers G J et al. *Vaccine.* 1989; 7(4):364-8; Vian L et al. *Toxic in Vitro.* 1995; 9(2):185-190; Parris N, et al. *Journal of the American Oil Chemists' Society.* 1973; 50(12):509-512; Germanaud L, et al. *Bulletin de la Société Chimique de France.* 1988; 4:699-704; EP 0569028 A; JP 2010-120998 A; U.S. Pat. No. 3,432,408; U.S. Pat. No. 4,085,134; U.S. Pat. No. 6,004,771; and CN 101456810 A.

It has surprisingly been found that the compounds of the present invention, in particular the compounds of formula 1, 2, 3, 4, 5 or 6 as described and defined herein below, have an advantageously low cytotoxicity. The present invention thus solves the problem of providing therapeutic agents having a favorable toxicity profile which are effective, inter alia, in the treatment, prevention or amelioration of inflammatory, autoimmune and/or allergic disorders.

Accordingly, the present invention provides a compound of the following formula 1

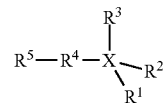

or a pharmaceutically acceptable salt, solvate or prodrug thereof for use in the treatment, prevention or amelioration of an inflammatory, autoimmune and/or allergic disorder which is selected from psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyositis, hyper-IgE (Buckley) syndrome, Wiskott-Aldrich syndrome, anaphylaxis, food allergy, allergic reactions to venomous stings, acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, urticaria angioedema, inflammatory bowel disease, Crohn's disease, ulcerative colitis, collagenous colitis, lymphocytic colitis, diversion colitis (diverticulitis), Behçet's syndrome, indeterminate colitis, celiac disease, irritable bowel syndrome, post-operative ileus, eosinophilic gastroenteropathy, gastritis, chronic allergic rhinitic, seasonal allergic rhinitis (hay-fever), allergic conjunctivitis, chemical conjunctivitis, neonatal conjunctivitis, Sjögren syndrome, open-angle glaucoma, dry eye disease (DED; including, e.g., aqueous tear-deficient dry eye (ADDE), Sjögren syndrome dry eye (SSDE), non-SSDE, or evaporative dry eye (EDE)), diabetic macular edema (or diabetic retinopathy), chronic obstructive pulmonary disease (COPD), allergic asthma, allergic bronchopulmonary aspergillosis, hypersensitivity pneumonitis, lung fibrosis, rheumatoid arthritis, juvenile rheumatoid arthritis, ankylosing spondylitis, systemic lupus erythematosus (SLE), scleroderma, reactive arthritis, polymyalgia rheumatica, Guillain-Barre syndrome, Hashimoto's thyroiditis, Grave's disease, temporal arteritis, primary biliary cirrhosis, sclerosing cholangitis, autoimmune hepatitis, alopecia areata, a graft-versus-host disease, a host-versus-graft disease, or a transplant rejection.

In formula 1, $R^1$ is a $C_{10-20}$ hydrocarbon group.

$R^2$ is a $C_{1-4}$ alkyl group, and $R^3$ is —H, a $C_{1-4}$ alkyl group or $R^3$ is absent.

Alternatively, $R^2$ and $R^3$ are mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —O($C_{1-3}$ alkyl), —O—C(O)—($C_{1-3}$ alkyl), $C_{1-3}$ alkyl, —NH$_2$, —NH($C_{1-3}$ alkyl) or —N($C_{1-3}$ alkyl)($C_{1-3}$ alkyl).

$R^4$ is a $C_{3-6}$ alkylene group which is substituted with one or more groups independently selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH.

$R^5$ is —SO$_3$—, —SO$_3$H, —PO$_3$H—, —PO$_3^{2-}$, —PO$_3$H$_2$, —PO$_2$(O$C_{1-3}$ alkyl)$^-$, —PO$_2$H(O$C_{1-3}$ alkyl), —PO(O$C_{1-3}$ alkyl)$_2$, —CO$_2^-$, —CO$_2$H or —CO$_2$($C_{1-3}$ alkyl).

X is N$^+$ or, if $R^3$ is absent, X is N.

The present invention also relates to a pharmaceutical composition comprising a compound of formula 1, as described and defined herein, or a pharmaceutically acceptable salt, solvate or prodrug thereof, and a pharmaceutically acceptable excipient for use in the treatment, prevention or amelioration of an inflammatory, autoimmune and/or allergic disorder which is selected from psoriasis, atopic dermatitis (atopic eczema), contact dermatitis, xerotic eczema, seborrheic dermatitis, neurodermitis, dyshidrosis, discoid eczema, vennus eczema, dermatitis herpetiformis (Duhring's Disease), autoeczematization, dermatomyositis, hyper-IgE (Buckley) syndrome, Wiskott-Aldrich syndrome, anaphylaxis, food allergy, allergic reactions to venomous stings, acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, urticaria angioedema, inflammatory bowel disease, Crohn's disease, ulcerative colitis, collagenous colitis, lymphocytic colitis, diversion colitis (diverticulitis), Behçet's syndrome, indeterminate colitis, celiac disease, irritable bowel syndrome, post-operative ileus, eosinophilic gastroenteropathy, gastritis, chronic allergic rhinitis, seasonal allergic rhinitis (hayfever), allergic conjunctivitis, chemical conjunctivitis, neonatal conjunctivitis, Sjögren syndrome, open-angle glaucoma, dry eye disease (DED; including, e.g., aqueous tear-deficient dry eye (ADDE), Sjögren syndrome dry eye (SSDE), non-SSDE, or evaporative dry eye (EDE)), diabetic macular edema (or diabetic retinopathy), chronic obstructive pulmonary disease (COPD), allergic asthma, allergic bronchopulmonary aspergillosis, hypersensitivity pneumonitis, lung fibrosis, rheumatoid arthritis, juvenile rheumatoid arthritis, ankylosing spondylitis, systemic lupus erythematosus (SLE), scleroderma, reactive arthritis, polymyalgia rheumatica, Guillain-Barre syndrome, Hashimoto's thyroiditis, Grave's disease, temporal arteritis, primary biliary cirrhosis, sclerosing cholangitis, autoimmune hepatitis, alopecia areata, a graft-versus-host disease, a host-versus-graft disease, or a transplant rejection.

The present invention further relates to a method of treating, preventing or ameliorating an inflammatory, autoimmune and/or allergic disorder, the method comprising the administration of a compound of formula 1, as described and defined herein, or a pharmaceutically acceptable salt, solvate or prodrug thereof, or a pharmaceutical composition comprising any of the aforementioned entities and a pharmaceutically acceptable excipient, to a subject (preferably, a human or a non-human mammal) in need of such a treatment, prevention or amelioration, wherein the inflammatory, autoimmune and/or allergic disorder is selected from psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyositis, hyper-IgE (Buckley) syndrome, Wiskott-Aldrich syndrome, anaphylaxis, food allergy, allergic reactions to venomous stings, acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, urticaria angioedema, inflammatory bowel disease, Crohn's disease, ulcerative colitis, collagenous colitis, lymphocytic colitis, diversion colitis (diverticulitis), Behçet's syndrome, indeterminate colitis, celiac disease, irritable bowel syndrome, post-operative ileus, eosinophilic gastroenteropathy, gastritis, chronic allergic rhinitis, seasonal allergic rhinitis (hayfever), allergic conjunctivitis, chemical conjunctivitis, neonatal conjunctivitis, Sjögren syndrome, open-angle glaucoma, dry eye disease (DED; including, e.g., aqueous tear-deficient dry eye (ADDE), Sjögren syndrome dry eye (SSDE), non-SSDE, or evaporative dry eye (EDE)), diabetic macular edema (or diabetic retinopathy), chronic obstructive pulmonary disease (COPD), allergic asthma, allergic bronchopulmonary aspergillosis, hypersensitivity pneumonitis, lung fibrosis, rheumatoid arthritis, juvenile rheumatoid arthritis, ankylosing spondylitis, systemic lupus erythematosus (SLE), scleroderma, reactive arthritis, polymyalgia rheumatica, Guillain-Barre syndrome, Hashimoto's thyroiditis, Grave's disease, temporal arteritis, primary biliary cirrhosis, sclerosing cholangitis, autoimmune hepatitis, alopecia areata, a graft-versus-host disease, a host-versus-graft disease, or a transplant rejection.

Allergic and inflammatory responses are characterized by dynamic interactions of immune and non-immune cells, coordinated through cell-cell contact and soluble immune mediators. These responses and their outcomes are further modified by each individual's genetics and lifestyle.

T helper cells play a key role in initiation and maintenance of inflammatory responses and can be divided into Th1 (cell-mediated immunity) and Th2 (antibody-mediated immunity) driven processes. Imbalances in these responses can result in pathological hyper- or hyposensitivity to antigens. A chronic inflammation manifests in diverse disease states such as, for instance, inflammatory bowel disease, rheumatoid arthritis, atopic dermatitis, urticaria and psoriasis.

Inflammatory responses to antigens can take the form of helper T cell driven responses of different types. Th1 cells mediate cellular responses involving cytotoxic cells such as macrophages, neutrophils and eosinophils, whereas Th2 cells mediate humoral responses involving secretion of antibodies from B cells and activation of mast cells. Other non-immune responses, such as those involving cyclooxygenase and lipoxygenase may also be involved. Uncontrolled release of cytokines and chemokines is at the heart of inflammatory diseases, like inflammatory bowel disease, rheumatoid arthritis, atopic dermatitis, urticaria and psoriasis.

A new interventional strategy is provided by the compounds according to the present invention, in particular the compounds of formula 1, 2, 3, 4, 5 or 6 as described and defined herein, which broadly modulate the activities of proteins within the inflammatory cascade. Through enrichment of the drug in membrane domains, an allosteric inhibition is exerted on key target proteins in signal transduction cascades in inflammation.

The compounds of the present invention were identified as potent inhibitors of immune mediator release in vitro in a mast cells model, as also demonstrated in Example 6. Furthermore, they inhibited release of the proinflammatory cytokines, TNF-α and interleukin-6, from peripheral blood mononuclear cells (PBMCs) stimulated with lipopolysaccharide, demonstrating immunomodulatory activity in different cell types.

Broad anti-inflammatory activity was confirmed in animal models of Th1 and Th2 driven inflammation. In a predominantly Th1-driven delayed type hypersensitivity (DTH) model in mice, the compounds suppressed the inflammatory response to an extent equivalent to dexamethasone, a marketed corticosteroid characterized by severe side effects, as shown in Example 8. In a predominantly Th2 driven allergic contact dermatitis model, the compounds were highly active after topical application and also showed an anti-inflammatory effect after oral administration, as shown in Example 9.

In the context of the present invention, it was surprisingly found that the compounds of formula 1, 2, 3, 4, 5 or 6 as described and defined herein are potent inhibitors of mast cell degranulation and thus function as mast cell stabilizers and/or potent inhibitors of allergic and/or cellular inflammation. In particular, it was surprisingly found that the compounds as disclosed herein can be used therapeutically in the treatment, prevention and/or amelioration of immunological disorders and disorders related to allergic and/or cellular inflammation, in particular inflammatory, autoimmune and/or allergic disorders.

T helper (Th) cells are a subgroup of lymphocytes that play an important role in the immune system due to their participation in activating and directing other immune cells. The other major types of lymphocytes are B cells and natural killer (NK) cells. During the antigenic activation and proliferation of Th cells, the Th0 cells differentiate into Th1, Th2 or other subtypes depending on the type of antigen, the antigen presenting cell and the cytokine environment.

Delayed type hypersensitivity, also called type IV hypersensitivity is an antibody-independent Th cell-mediated immune memory response resulting from an over-stimulation of immune cells, commonly lymphocytes and macrophages, resulting in chronic inflammation and cytokine release. Important disease examples are contact dermatitis, chronic inflammation of ileum and colon, e.g. as seen in inflammatory bowel disease (IBD), rheumatoid arthritis and related diseases, ankylosing spondylitis, systemic lupus erythematosus, scleroderma, Gaucher's disease, fibromyalgia, osteoarthritis, reactive arthritis, pelvic inflammatory disease, polymyalgia rheumatica, multiple sclerosis, Guillain-Barre syndrome, Hashimoto's thyroiditis, Grave's disease, and chronic transplant rejection. For IBD, for instance, Hue et al. demonstrated a causal relationship between the disease and T cell-mediated intestinal inflammation (Hue, S; et al. (2006) J. Exp. Med. 203 (11), 2473).

Psoriasis is a chronic autoimmune disease affecting the skin. One hypothesis for the cause of psoriasis sees the disease as being an immune-mediated disorder in which the excessive reproduction of skin cells is secondary to factors produced by the immune system. T cells become active, migrate to the dermis and trigger the release of cytokines which cause inflammation and the rapid production of skin cells.

Mast cells, or mastocytes, play a key role in the inflammatory process. When activated, the mast cell rapidly releases its characteristic granules and various hormonal mediators into the the interstitium, a process called degranulation. The molecules released into the extracellular environment include preformed mediators, e.g. histamine and serotonin, newly formed lipid mediators (eicosanoids) and cytokines. In allergic reactions, mast cells remain inactive until an allergen binds to the IgE receptor expressed at the cell surface, leading to degranulation and release of mediators.

Many forms of cutaneous and mucosal allergies, in most cases accompanied by inflammatory symptoms, are mediated largely by mast cells. They play a central role in asthma, eczema, itch and the various forms of rhinitis, conjunctivitis and urticaria. Mast cells are also implicated in the pathology associated with disorders such as rheumatoid arthritis, bullous pemphigoid and multiple sclerosis. They have been shown to be involved in the recruitment of inflammatory cells to the joints and skin. Moreover, mastocytosis is a disorder featuring proliferation of mast cells and exists in a cutaneous and systemic form.

Atopic dermatitis, also known as neurodermitis, is an inflammatory and pruritic skin disorder characterised by chronic inflammation. Although the causes underlying atopic dermatitis are not well understood and the relationships between intake of, or contact with, allergens and various inflammatory stimuli are not well established, it is postulated that mast cell and/or T cell-related processes are involved in the pathological processes leading to atopic dermatitis.

Asthma and chronic obstructive pulmonary disease (COPD) are both obstructive airway disorders, but differing types of inflammation are involved in the pathogenesis of these diseases. Asthma is frequently an allergic process with a preponderance of Th2 cells and eosinophils in the airways. In contrast, there is predominant Th1 activity in the blood of COPD patients (Lecki, M J; et al. (2003) Thorax 58, 23).

Dry eye disease (DED) is an inflammatory disorder of the lacrimal functional unit leading to chronic ocular surface disease, impaired quality of vision, and a wide ranae of complications. It is recognized that a chronic inflammatory response plays a key role in the pathogenesis of human dry eye disease (Calonge M, et al. Ocul Immunol Inflamm. 2010. 18:244-253; Stevenson W, et al. Arch Ophthalmol. 2012. 130:90-100; Zoukhri D. Exp Eye Res. 2006. 82:885-898; Pflugfelder S C. Am J Ophthalmol. 2004. 137:337-342).

Diabetic macular edema (or diabetic retinopathy) is characterized by early retinal microvascular dysfunction and is a leading cause of blindness in subjects suffering from diabetes. There is evidence indicating that retinal inflammation plays an important role in the pathogenesis of diabetic macular edema (Joussen A M, et al. FASEBJ. 2004. 18:1450-1452; Rangasamy S, et al. Middle East Afr J Ophthalmol. 2012. 19:52-59; Meleth A D, et al. Invest Ophthalmol Vis Sci. 2005. 46:4295-4301; Funatsu H, et al. Ophthalmology. 2009. 116:73-79; Kim S J, et al. Sury Ophthalmol. 2010. 55:108-133).

Accordingly, the compounds of the present invention, in particular the compounds of formula 1, 2, 3, 4, 5 or 6, are useful in the treatment, prevention or amelioration of an inflammatory, autoimmune and/or allergic disorder.

The inflammatory, autoimmune and/or allergic disorder to be treated, prevented or ameliorated using the compounds of formula 1 or 2 according to the invention is selected from: psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyositis, hyper-IgE (Buckley) syndrome, Wiskott-Aldrich syndrome, anaphylaxis, food allergy, or allergic reactions to venomous stings; acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, or urticaria angioedema; inflammatory bowel disease, Crohn's disease, ulcerative colitis, collagenous colitis, lymphocytic colitis, diversion colitis (diverticulitis), Behçet's syndrome, indeterminate colitis, celiac disease, irritable bowel syndrome, post-operative ileus, eosinophilic gastroenteropathy, or gastritis; chronic allergic rhinitis, seasonal allergic rhinitis (hay-fever), allergic conjunctivitis, chemical conjunctivitis, neonatal conjunctivitis, Sjögren syndrome, open-angle glaucoma, dry eye disease (DED; including, e.g., aqueous tear-deficient dry eye (ADDE), Sjögren syndrome dry eye (SSDE), non-SSDE, or evaporative dry eye (EDE)), or diabetic macular edema (or diabetic retinopathy); chronic obstructive pulmonary disease (COPD), allergic asthma, allergic bronchopulmonary aspergillosis, hypersensitivity pneumonitis, or lung fibrosis; rheumatoid arthritis, juvenile rheumatoid arthritis, ankylosing spondylitis, systemic lupus erythematosus (SLE), scleroderma, reactive arthritis, or polymyalgia rheumatica; Guillain-Barre syndrome, Hashimoto's thyroiditis, Grave's disease, temporal arteritis, primary biliary cirrhosis, sclerosing cholangitis, autoimmune hepatitis, or alopecia areata; or a graft-versus-host disease, a host-versus-graft disease or a transplant rejection.

Furthermore, the compounds of the present invention, in particular the compounds of formula 1, 2, 3, 4, 5 or 6, have been demonstrated to be effective in the inhibition of Akt kinase activation, as also shown in Example 7, and are thus useful in the treatment, prevention or amelioration of proliferative, neoplastic or dysplastic diseases or disorders, which will be described in more detail in the following.

Evidence indicates that Akt plays a key role in cancer progression by stimulating cell proliferation and inhibiting apoptosis (Chen et al., Cell Mol Immunol. 2:241-52 (2005)). Unregulated activation of the PI3K/Akt pathway commonly occurs in cancer through a variety of mechanisms, including genetic mutations of kinases and regulatory proteins, epigenetic alterations that alter gene expression and translation, and posttranslational modifications. Analysis of Akt levels in human tumors showed that Akt is overexpressed in a significant number of ovarian (Cheng et al., Proc Natl Acad Sci USA. 89:9267-9271(1992)), pancreatic (Cheng et al., Proc Natl Acad Sci USA. 93:3636-3641 (1996)), breast and prostate cancers (Nakatani et al., J Biol Chem. 274:21528-21532 (1999)) and thyroid tumors (Saji and Ringel, Mol Cell Endocrinol. 321:20-8 (2010). These observations demonstrate that the PI3K/Akt pathway plays important roles for regulating cell survival or apoptosis in tumorgenesis. Constitutive activation of the PI3K/Akt pathway promotes the long-term survival and outgrowth of cancer cells. The compounds of the present invention, which are inhibitors of Akt kinase activation, are thus envisaged to be used in the treatment, prevention or amelioration of a proliferative, neoplastic or dysplastic disease or disorder, particularly cancer.

The compounds of the invention, which have been demonstrated to exhibit an efficacy in the suppression of the inflammatory response at least equivalent to that of the corticosteroid dexamethasone, as also shown in Examples 8 and 9, are furthermore advantageous in that they do not show the adverse effects observed for corticosteroids, such as reduction of lymph node weight and cell number which was observed for the corticosteroid diflorasone in Example 9, which makes them particularly useful in the treatment, prevention or amelioration of inflammatory, autoimmune and/or allergic disorders.

Moreover, the compounds of the present invention, including the compounds of formula 1, 2, 3, 4, 5 or 6, have a particularly low cytotoxicity and, thus, an advantageous toxicity profile, as also demonstrated in Example 6.

The compound of formula 1 as defined above is described in more detail in the following.

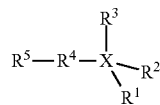

$R^1$ is a $C_{10-20}$ hydrocarbon group. Preferably, $R^1$ is an alkyl group, an alkenyl group, or an alkynyl group; more preferably. $R^1$ is a linear alkyl group, a linear alkenyl group, or a linear alkynyl group; even more preferably, $R^1$ is a linear alkyl group. The number of carbon atoms of the hydrocarbon group, the alkyl group, the alkenyl group, or the alkynyl group is 10 to 20, preferably 12, 14 or 16. Accordingly, it is particularly preferred that $R^1$ is —$(CH_2)_{11}$—$CH_3$, —$(CH_2)_{13}$—$CH_3$, or —$(CH_2)_{15}$—$CH_3$.

$R^2$ is a $C_{1-4}$ alkyl group, and $R^3$ is —H, a $C_{1-4}$ alkyl group or $R^3$ is absent; or $R^2$ and $R^3$ are mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —O—C(O)—($C_{1-3}$ alkyl), $C_{1-3}$ alkyl, —$NH_2$, —$NH(C_{1-3}$ alkyl) or —$N(C_{1-3}$ alkyl)($C_{1-3}$ alkyl).

In one preferred embodiment, $R^2$ is methyl, and $R^3$ is —H, a $C_{1-4}$ alkyl group or $R^3$ is absent. More preferably, $R^2$ is methyl, and $R^3$ is —H, methyl or $R^3$ is absent. Even more preferably. $R^2$ is methyl and $R^3$ is methyl.

In another preferred embodiment, $R^2$ and $R^3$ are mutually linked to form a pyrrolidine ring, a piperidine ring or an azepane ring together with the nitrogen atom X to which they are attached. More preferably, $R^2$ and $R^3$ are mutually linked to form a piperidine ring together with the nitrogen atom X to which they are attached. The pyrrolidine ring, the piperidine ring or the azepane ring may be substituted with one or more (such as, e.g., one, two, three, or four), preferably one or two, more preferably one, groups independently selected from —OH, —O($C_{1-3}$ alkyl), —O—C(O)—($C_{1-3}$ alkyl), $C_{1-3}$ alkyl, —$NH_2$, —$NH(C_{1-3}$ alkyl) or —$N(C_{1-3}$ alkyl)($C_{1-3}$ alkyl). Preferably, the pyrrolidine ring, the piperidine ring or the azepane ring is unsubstituted or substituted with one group —OH. Accordingly, it is particularly preferred that $R^2$ and $R^3$ are mutually linked to form a piperidine ring together with the nitrogen atom X to which they are attached, wherein the piperidine ring is optionally substituted with one group —OH, preferably in para position with respect to the nitrogen atom X.

$R^4$ is a $C_{3-6}$ alkylene group, which is substituted with one or more (such as, e.g., one, two, three, or four) groups, preferably one or two groups, more preferably one group, independently selected from —OH, —O($C_{1-3}$ alkyl), —O—C(O)—($C_{1-3}$ alkyl), —O—C(O)—O($C_{1-3}$ alkyl), —O—C(O)—$NH_2$, —O—C(O)—$NH(C_{1-3}$ alkyl), —O—C(O)—$N(C_{1-3}$ alkyl)($C_{1-3}$ alkyl), —O($CH_2)_2OH$, or —O($CH_2)_3OH$. The alkylene group may be linear or branched; preferably, the alkylene group is linear. The alkylene group has 3 to 6 (i.e., 3, 4, 5 or 6) carbon atoms, and preferably has 3 carbon atoms. The one or more groups with which the alkylene group is substituted is/are preferably selected independently from —OH, —O($C_{1-3}$ alkyl), —O—C(O)—($C_{1-3}$ alkyl), —O—C(O)—O($C_{1-3}$ alkyl), —O($CH_2)_2OH$, or —O($CH_2)_3OH$. More preferably, the one or more groups with which the alkylene group is substituted is/are selected independently from —OH, —O—C(O)—($C_{1-3}$ alkyl), —O($CH_2)_2OH$, or —O($CH_2)_3OH$. It is particularly preferred that $R^4$ is —$(CH_2)_p$—$CH$(—$R^{41}$)—$CH_2$—, wherein the moiety —$(OH_2)_p$— within the group —$(CH_2)_p$—$CH$(—$R^{41}$)—$CH_2$— is connected to $R^5$, p is an integer from 1 to 4 (i.e., 1, 2, 3 or 4; preferably, p is 1), and $R^{41}$ is selected from —OH, —O($C_{1-3}$ alkyl), —O—C(O)—($C_{1-3}$ alkyl), —O—C(O)—O($C_{1-3}$ alkyl), —O—C(O)—$NH_2$, —O—C(O)—$NH(C_{1-3}$ alkyl), —O—C(O)—

$N(C_{1-3}$ alkyl$)(C_{1-3}$ alkyl), —O(CH$_2$)$_2$OH, or —O(CH$_2$)$_3$OH, preferably from —OH, —O(C$_{1-3}$ alkyl), —O—C(O)—(C$_{1-3}$ alkyl), —O—C(O)—O(C$_{1-3}$ alkyl), —O(CH$_2$)$_2$OH, or —O(CH$_2$)$_3$OH, and more preferably from —OH, —O—C(O)—(C$_{1-3}$ alkyl), —O(CH$_2$)$_2$OH, or —O(CH$_2$)$_3$OH. Even more preferably, $R^4$ is —CH$_2$—CH(—R$^{41}$)—CH$_2$—, wherein $R^{41}$ is selected from —OH, —O(C$_{1-3}$ alkyl), —O—C(O)—(C$_{1-3}$ alkyl), —O—C(O)—O(C$_{1-3}$ alkyl), —O—C(O)—NH$_2$, —O—C(O)—NH(C$_{1-3}$ alkyl), —O—C(O)—N(C$_{1-3}$ alkyl)(C$_{1-3}$ alkyl), —O(CH$_2$)$_2$OH, or —O(CH$_2$)$_3$OH, preferably from —OH, —O(C$_{1-3}$ alkyl), —O—C(O)—(C$_{1-3}$ alkyl), —O(CH$_2$)$_2$OH, or —O(CH$_2$)$_3$OH, and more preferably from —OH, —O—C(O)—(C$_{1-3}$ alkyl) or —O(CH$_2$)$_2$OH. Yet even more preferably, $R^4$ is —CH$_2$—CH(—OH)—CH$_2$— or —CH$_2$—CH(—O—C(O)—(C$_{1-3}$ alkyl))—CH$_2$—.

$R^5$ is —SO$_3^-$, —SO$_3$H, —PO$_3$H$^-$, —PO$_3^{2-}$, —PO$_3$H$_2$, —PO$_2$(OC$_{1-3}$ alkyl)$^-$, —PO$_2$H(OC$_{1-3}$ alkyl), —PO(OC$_{1-3}$ alkyl)$_2$, —CO$_2^-$, —CO$_2$H, or —CO$_2$(C$_{1-3}$ alkyl). Preferably, $R^5$ is —SO$_3^-$, —SO$_3$H, —PO$_3$H$^-$, —PO$_3^{2-}$, or —PO$_3$H$_2$. In one preferred embodiment, $R^5$ is —SO$_3^-$ or —SO$_3$H. In another preferred embodiment, $R^5$ is —PO$_3^{2-}$, —PO$_3$H$^-$, or —PO$_3$H$_2$.

X is $N^+$ or, if $R^3$ is absent, X is N.

A person skilled in the art understands that, if the compound of formula 1 is provided in solution, the protonation of the acid group $R^5$ depends on the pH of the solution. For example, if $R^5$ is —PO$_3$H—, it may be present as —PO$_3$H$_2$ in a more acidic environment or as —PO$_3^{2-}$ in a more alkaline environment.

Likewise, a skilled person understands that, if the compound of formula 1 is provided in solution and if $R^3$ in formula 1 is —H or is absent, the protonation of the nitrogen atom X and, accordingly, the charge at the nitrogen atom X depends on the pH of the solution. Thus, depending on the pH of the solution, $R^3$ may be —H and X may be $N^+$, or $R^3$ may be absent and X may be N.

Preferred examples of the compound of formula 1 are the compounds 1a, 1b, 1c, 1d or 1e shown below or pharmaceutically acceptable salts, solvates or prodrugs thereof:

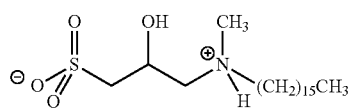

1a

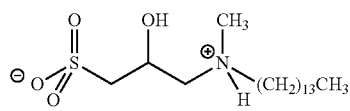

1b

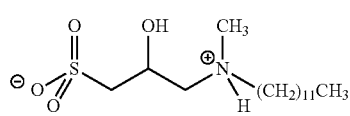

1c

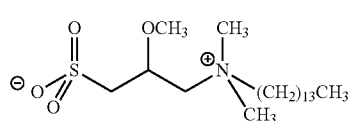

1d

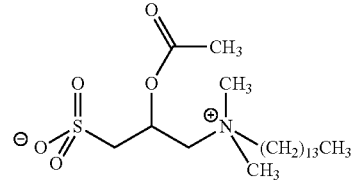

1e

In one embodiment described above, $R^2$ and $R^3$ in formula 1 are mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —O(C$_{1-3}$ alkyl), —O—C(O)—(C$_{1-3}$ alkyl), C$_{1-3}$ alkyl, —NH$_2$, —NH(C$_{1-3}$ alkyl) or —N(C$_{1-3}$ alkyl)(C$_{1-3}$ alkyl).

Accordingly, the compound of formula 1 may be a compound of the following formula 2

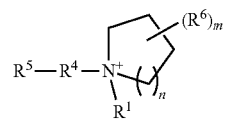

2 or a pharmaceutically acceptable salt, solvate or prodrug thereof.

In formula 2, the groups $R^1$, $R^4$, and $R^5$ have the meanings or the preferred meanings defined herein above for the compound of formula 1.

n is 1, 2, or 3. Preferably, n is 2.

m is an integer from 0 to 4. Preferably, m is 0, 1, or 2; more preferably, m is 0 or 1; even more preferably, m is 1.

Each $R^6$ is independently selected from —OH, —O(C$_{1-3}$ alkyl), —O—C(O)—(C$_{1-3}$ alkyl), C$_{1-3}$ alkyl, —NH$_2$, —NH(C$_{1-3}$ alkyl) or —N(C$_{1-3}$ alkyl)(C$_{1-3}$ alkyl). Preferably, each $R^6$ is —OH.

It is to be understood that each $R^6$ is attached to a carbon atom of the pyrrolidine, piperidine or azepane ring. It is further to be understood that, if m is 0, the pyrrolidine, piperidine or azepane ring (to which $R^6$ would be attached) is unsubstituted, i.e. is substituted with hydrogen.

In one embodiment, n is 1 or 3, and m is 0.

In a preferred embodiment, n is 2, m is 1, and $R^6$ is —OH, —O(C$_{1-3}$ alkyl), —O—C(O)—(C$_{1-3}$ alkyl), C$_{1-3}$ alkyl, —NH$_2$, —NH(C$_{1-3}$ alkyl) or —N(C$_{1-3}$ alkyl)(C$_{1-3}$ alkyl), in particular —OH. In this embodiment, it is further preferred that $R^6$ is in para position in respect of the ring nitrogen atom $N^+$.

The invention furthermore relates to a compound of formula 3 or a pharmaceutically acceptable salt, solvate or prodrug thereof for use as a medicament.

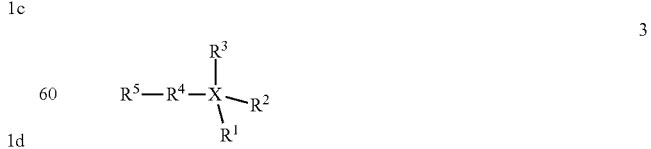

3

In formula 3, the groups $R^1$, $R^2$, $R^3$, $R^5$, and X have the same meanings and preferred meanings as described and defined herein above for the corresponding groups in formula 1.

Accordingly, $R^2$ in formula 3 is a $C_{1-4}$ alkyl group, and $R^3$ is —H, a $C_{1-4}$ alkyl group or $R^3$ is absent; or $R^2$ and $R^3$ are mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —O($C_{1-3}$ alkyl), —O—C(O)—($C_{1-3}$ alkyl), $C_{1-3}$ alkyl, —NH$_2$, —NH($C_{1-3}$ alkyl) or —N($C_{1-3}$ alkyl)($C_{1-3}$ alkyl).

If $R^2$ and $R^3$ are not mutually linked, then $R^4$ in formula 3 is —CH$_2$—CH(—OH)—CH$_2$— or $R^4$ is a $C_{3-6}$ alkylene group which is substituted with one or more groups independently selected from —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH or —O(CH$_2$)$_3$OH. If $R^2$ and $R^3$ are mutually linked to form a pyrrolidine ring, a piperidine ring or an azepane ring together with the nitrogen atom X to which they are attached, then $R^4$ in formula 3 is a $C_{3-6}$ alkylene group which is substituted with one or more groups independently selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH or —O(CH$_2$)$_3$OH.

Accordingly, if $R^2$ and $R^3$ are not mutually linked, $R^4$ in formula 3 is —CH$_2$—CH(—OH)—CH$_2$— or $R^4$ is a $C_{3-6}$ alkylene group, wherein said $C_{3-6}$ alkylene group is substituted with one or more (such as, e.g., one, two, three, or four) groups, preferably one or two groups, more preferably one group, independently selected from —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH. The alkylene group may be linear or branched; preferably, the alkylene group is linear. The alkylene group has 3 to 6 (i.e., 3, 4, 5 or 6) carbon atoms, and preferably has 3 carbon atoms. The one or more groups with which the alkylene group is substituted is/are preferably selected independently from —O($C_{1-3}$ alkyl), —O—C(O)—($C_{1-3}$ alkyl), —O—C(O)—O($C_{1-3}$ alkyl), —O(OH$_2$)$_2$OH, or —O(CH$_2$)$_3$OH. More preferably, the one or more groups with which the alkylene group is substituted is/are selected independently from —O—C(O)—($C_{1-3}$ alkyl), —O(CH$_2$)$_2$OH, or —O(CH$_2$)$_3$OH. It is particularly preferred that $R^4$ is —CH$_2$—CH(—OH)—CH$_2$— or —(CH$_2$)$_p$—CH(—R$^{41}$)—CH$_2$—, wherein the moiety —(CH$_2$)$_p$— within the group —(CH$_2$)$_p$—CH(—R$^{41}$)—CH$_2$— is connected to $R^5$, p is an integer from 1 to 4 (i.e., 1, 2, 3 or 4; preferably, p is 1), and $R^{41}$ is selected from —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH, preferably from —O($C_{1-3}$ alkyl), —O—C(O)—($C_{1-3}$ alkyl), —O—C(O)—O($C_{1-3}$ alkyl), —O(CH$_2$)$_2$OH, or —O(CH$_2$)$_3$OH, and more preferably from —O—C(O)—($C_{1-3}$ alkyl), —O(CH$_2$)$_2$OH, or —O(CH$_2$)$_3$OH. Yet even more preferably, $R^4$ is —CH$_2$—CH(—OH)—CH$_2$— or —CH$_2$—CH(—O—C(O)—($C_{1-3}$ alkyl))—OH$_2$—.

If $R^2$ and $R^3$ are mutually linked to form a pyrrolidine ring, a piperidine ring or an azepane ring together with the nitrogen atom X to which they are attached, then $R^4$ in formula 3 is a $C_{3-6}$ alkylene group, which is substituted with one or more (such as, e.g., one, two, three, or four) groups, preferably one or two groups, more preferably one group, independently selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH. The alkylene group may be linear or branched; preferably, the alkylene group is linear. The alkylene group has 3 to 6 (i.e., 3, 4, 5 or 6) carbon atoms, and preferably has 3 carbon atoms. The one or more groups with which the alkylene group is substituted is/are preferably selected independently from —OH, —O($C_{1-3}$ alkyl), —O—C(O)—($C_{1-3}$ alkyl), —O—C(O)—O($C_{1-3}$ alkyl), —O(CH$_2$)$_2$OH, or —O(CH$_2$)$_3$OH. More preferably, the one or more groups with which the alkylene group is substituted is/are selected independently from —OH, —O—C(O)—($C_{1-3}$ alkyl), —O(CH$_2$)$_2$OH, or —O(CH$_2$)$_3$OH. It is particularly preferred that $R^4$ is —(OH$_2$)$_p$—CH(—R$^{41}$)—CH$_2$—, wherein the moiety —(CH$_2$)$_p$— within the group —(CH$_2$)$_p$—CH(—R$^{41}$)—CH$_2$— is connected to $R^5$, p is an integer from 1 to 4 (i.e., 1, 2, 3 or 4; preferably, p is 1), and $R^{41}$ is selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH, preferably from —OH, —O($C_{1-3}$ alkyl), —O—C(O)—($C_{1-3}$ alkyl), —O—C(O)—O($C_{1-3}$ alkyl), —O(CH$_2$)$_2$OH, or —O(CH$_2$)$_3$OH, and more preferably from —OH, —O—C(O)—($C_{1-3}$ alkyl), —O(CH$_2$)$_2$OH, or —O(CH$_2$)$_3$OH. Even more preferably, $R^4$ is —CH$_2$—CH(—R$^{41}$)—CH$_2$—, wherein $R^{41}$ is selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH, preferably from —OH, —O($C_{1-3}$ alkyl), —O—C(O)—($C_{1-3}$ alkyl), —O(CH$_2$)$_2$OH, or —O(CH$_2$)$_3$OH, and more preferably from —OH, —O—C(O)—($C_{1-3}$ alkyl) or —O(CH$_2$)$_2$OH. Yet even more preferably, $R^4$ is —CH$_2$—CH(—OH)—CH$_2$— or —CH$_2$—CH(—O—C(O)—($C_{1-3}$ alkyl))—OH$_2$—.

Preferred examples of the compound of formula 3 are the compounds 1a, 1b, 1c, 1d or 1e shown below or pharmaceutically acceptable salts, solvates or prodrugs thereof:

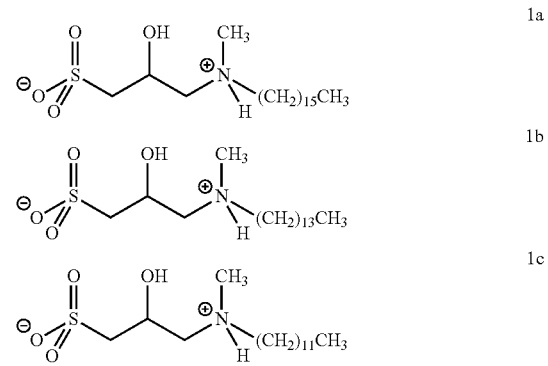

-continued

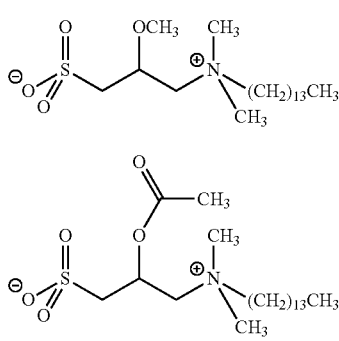

In accordance with the above definition of the compound of formula 3, the groups $R^2$ and $R^3$ may, in one embodiment, be mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —O($C_{1-3}$ alkyl), —O—C(O)—($C_{1-3}$ alkyl), $C_{1-3}$ alkyl, —$NH_2$, —NH($C_{1-3}$ alkyl) or —N($C_{1-3}$ alkyl)($C_{1-3}$ alkyl).

The compound of formula 3, which is provided herein as a medicament, may thus be a compound of the following formula 4

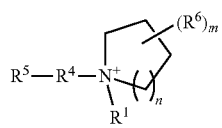

or a pharmaceutically acceptable salt, solvate or prodrug thereof.

The groups $R^1$ and $R^5$ in formula 4 have the same meanings and preferred meanings as defined herein above for the corresponding groups in formula 3.

In formula 4, n is 1, 2, or 3. Preferably, n is 2.

m is an integer from 0 to 4. Preferably, m is 0, 1, or 2; more preferably, m is 0 or 1; even more preferably, m is 1.

$R^4$ in formula 4 is a $C_{3-6}$ alkylene group which is substituted with one or more (such as, e.g., one, two, three, or four) groups, preferably one or two groups, more preferably one group, independently selected from —OH, —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2)_2$OH, or —O($CH_2)_3$OH. The alkylene group may be linear or branched; preferably, the alkylene group is linear. The alkylene group has 3 to 6 (i.e., 3, 4, 5 or 6) carbon atoms, and preferably has 3 carbon atoms. The one or more groups with which the alkylene group is substituted is/are preferably selected independently from —OH, —O($C_{1-3}$ alkyl), —O—C(O)—($C_{1-3}$ alkyl), —O—C(O)—O($C_{1-3}$ alkyl), —O($CH_2)_2$OH, or —O($CH_2)_3$OH. More preferably, the one or more groups with which the alkylene group is substituted is/are selected independently from —OH, —O—C(O)—($C_{1-3}$ alkyl), —O($CH_2)_2$OH, or —O($CH_2)_3$OH. It is particularly preferred that $R^4$ is —($CH_2)_p$—CH(—$R^{41}$)—$CH_2$—, wherein the moiety —($CH_2)_p$— within the group —($CH_2)_p$—CH(—$R^{41}$)—$CH_2$— is connected to $R^5$, p is an integer from 1 to 4 (i.e., 1, 2, 3 or 4; preferably, p is 1), and $R^{41}$ is selected from —OH, —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2)_2$OH, or —O($CH_2)_3$OH, preferably from —OH, —O($C_{1-3}$ alkyl), —O—C(O)—($C_{1-3}$ alkyl), —O—C(O)—O($C_{1-3}$ alkyl), —O($CH_2)_2$OH, or —O($CH_2)_3$OH, and more preferably from —OH, —O—C(O)—($C_{1-3}$ alkyl), —O($CH_2)_2$OH, or —O($CH_2)_3$OH. Even more preferably, $R^4$ is —$CH_2$—CH(—$R^{41}$)—$CH_2$—, wherein $R^{41}$ is selected from —OH, —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2)_2$OH, or —O($CH_2)_3$OH, preferably from —OH, —O($C_{1-3}$ alkyl), —O—C(O)—($C_{1-3}$ alkyl), —O($CH_2)_2$OH, or —O($CH_2)_3$OH, and more preferably from —OH, —O—C(O)—($C_{1-3}$ alkyl) or —O($CH_2)_2$OH. Yet even more preferably, $R^4$ is —$CH_2$—CH(—OH)—$CH_2$— or —$CH_2$—CH(—O—C(O)—($C_{1-3}$ alkyl))—$CH_2$—.

Each $R^6$ in formula 4 is independently selected from —OH, —O($C_{1-3}$ alkyl), —O—C(O)—($C_{1-3}$ alkyl), $C_{1-3}$ alkyl, —$NH_2$, —NH($C_{1-3}$ alkyl) or —N($C_{1-3}$ alkyl)($C_{1-3}$ alkyl). Preferably, each $R^6$ is —OH.

It is to be understood that each $R^6$ is attached to a carbon atom of the pyrrolidine, piperidine or azepane ring. It is further to be understood that, if m is 0, the pyrrolidine, piperidine or azepane ring (to which $R^6$ would be attached) is unsubstituted, i.e. is substituted with hydrogen.

In one embodiment, n is 1 or 3, and m is 0.

In a preferred embodiment, n is 2, m is 1, and $R^6$ is —OH, —O($C_{1-3}$ alkyl), —O—C(O)—($C_{1-3}$ alkyl), $C_{1-3}$ alkyl, —$NH_2$, —NH($C_{1-3}$ alkyl) or —N($C_{1-3}$ alkyl)($C_{1-3}$ alkyl), in particular —OH. In this embodiment, it is further preferred that $R^6$ is in para position in respect of the ring nitrogen atom $N^+$.

The present invention also relates to a pharmaceutical composition comprising a compound of formula 3 or 4, as described and defined herein, or a pharmaceutically acceptable salt, solvate or prodrug thereof, and a pharmaceutically acceptable excipient.

The invention further relates to a compound of formula 3 or 4, as described and defined herein, or a pharmaceutically acceptable salt, solvate or prodrug thereof, or a pharmaceutical composition comprising any of the aforementioned entities and a pharmaceutically acceptable excipient, for use in the treatment, prevention or amelioration of an inflammatory, autoimmune and/or allergic disorder.

Moreover, the present invention relates to a method of treating, preventing or ameliorating a disease or disorder, in particular an inflammatory, autoimmune and/or allergic disorder, the method comprising the administration of a compound of formula 3 or 4, as described and defined herein, or a pharmaceutically acceptable salt, solvate or prodrug thereof, or a pharmaceutical composition comprising any of the aforementioned entities and a pharmaceutically acceptable excipient, to a subject (preferably, a human or a non-human mammal) in need of such a treatment, prevention or amelioration.

The inflammatory, autoimmune and/or allergic disorder to be treated, prevented or ameliorated using the compounds of formula 3 or 4 according to the invention is, for example, selected from: psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyositis, hyper-IgE (Buckley) syndrome, Wiskott-Aldrich syndrome, anaphylaxis, food allergy, or allergic reactions to venomous stings; acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, or urticaria angioedema; inflammatory bowel disease, Crohn's disease, ulcerative colitis, collagenous colitis, lymphocytic colitis, diversion colitis (diverticulitis), Behçet's syndrome, indeterminate colitis, celiac disease, irritable bowel syndrome, post-operative ileus, eosinophilic gastroenteropathy, or gastritis; chronic allergic rhinitis, seasonal allergic rhinitis (hay-fever), allergic conjunctivitis, chemical conjunctivitis, neonatal conjunctivitis, Sjögren syndrome, open-angle glaucoma, dry eye disease (DED; including, e.g., aqueous tear-deficient dry eye (ADDE), Sjögren syndrome dry eye (SSDE), non-SSDE, or evaporative dry eye (EDE)), or diabetic macular edema (or diabetic retinopathy); chronic obstructive pulmonary disease (COPD), allergic asthma, allergic bronchopulmonary aspergillosis, hypersensitivity pneumonitis, or lung fibrosis; rheumatoid arthritis, juvenile rheumatoid arthritis, ankylosing spondylitis, systemic lupus erythematosus (SLE), scleroderma, osteoarthritis, reactive arthritis, or polymyalgia rheumatica; multiple sclerosis, Guillain-Barre syndrome, Hashimoto's thyroiditis, Grave's disease, temporal arteritis, primary biliary cirrhosis, sclerosing cholangitis, autoimmune hepatitis, alopecia areata or autoimmune lymphoproliferative syndrome (ALPS); a graft-versus-host disease, a host-versus-graft disease or a transplant rejection; or an inflammatory contribution to Alzheimer's disease or Parkinson's disease.

Furthermore, the invention relates to a compound of formula 3 or 4 or a pharmaceutically acceptable salt, solvate or prodrug thereof, or a pharmaceutical composition comprising any of the aforementioned entities and a pharmaceutically acceptable excipient, for use in the treatment, prevention or amelioration of a proliferative, neoplastic or dysplastic disease or disorder. The invention also encompasses a method of treating, preventing or ameliorating a proliferative, neoplastic or dysplastic disease or disorder, the method comprising the administration of a compound of formula 3 or 4 or a pharmaceutically acceptable salt, solvate or prodrug thereof, or a pharmaceutical composition comprising any of the aforementioned entities and a pharmaceutically acceptable excipient, to a subject (preferably, a human or a non-human mammal) in need of such a treatment, prevention or amelioration.

The proliferative, neoplastic or dysplastic disease or disorder to be treated, prevented or ameliorated using a compound of formula 3 or 4 according to the invention is, for example, a benign or malignant neoplasia, such as, e.g., leukemia, adrenocortical carcinoma, an AIDS-related cancer, appendix cancer, astrocytoma, basal cell carcinoma, bile duct cancer, bladder cancer, bone cancer, brain tumor, breast cancer, a bronchial adenoma, Burkitt lymphoma, carcinoid tumor, central nervous system lymphoma, cerebellar astrocytoma, cervical cancer, colon cancer, cutaneous T-cell lymphoma, chronic lymphovytic leukemia, chronic myelogenous leukemia, a chronic myeloproliferative disorder, desmoplastic small round cell tumor, endometrial cancer, ependymoma, esophageal cancer, Ewing's sarcoma, extracranial germ cell tumor, extrahepatic bile duct cancer, intraocular melanoma, retinoblastoma, gallbladder cancer, gastric cancer, gastric carcinoid, gastrointestinal carcinoid tumor, gastrointestinal stromal tumor, germ cell tumor, glioma, gestational trophoblastic tumor, head and neck cancer, heart cancer, hepatocellular cancer, Hodgkin lymphoma, Non-Hodgkin lymphoma, hypopharyngeal cancer, hypthalamic and visual pathway glioma, intraocular melanoma, islet cell carcinoma, Kaposi sarcoma, renal cell cancer, laryngeal cancer, lip and oral cavity cancer, lung cancer, Waldenstrom's macroglobulinemia, osteosarcoma, medulloblastoma, melanoma, Merkel cell carcinoma, mesothelioma, mouth cancer, multiple endocrine neoplasia syndrome, plasma cell neoplasm, mycosis fungoides, a myelodysplastic disease, multiple myeloma, a myeloproliferative disorder, nasal cavity and paranasal sinus cancer, nasopharyngeal carcinoma, neuroblastoma, oral cancer, oropharyngeal cancer, ovarian cancer, ovarian epithelial cancer, ovarian germ cell tumor, pancreatic tumor, parathyroid cancer, penile cancer, pharyngeal cancer, pheochromocytoma, pineal astrocytoma, pineal germinoma, pineoblastoma, pituitary adenoma, pleuropulmonary blastoma, prostate cancer, rectal cancer, transitional cell cancer, rhabdomyosarcoma, salivary gland cancer, Szary syndrome, skin cancer, small cell lung cancer, small intestine cancer, soft tissue sarcoma, stomach cancer, supratentorial primitive neuroectodermal tumor, testicular cancer, throat cancer, thymoma, thyroid cancer, uterine cancer, uterine sarcoma, vaginal cancer, vulvar cancer, or Wilms tumor.

The invention furthermore provides novel compounds. These compounds are described herein and are characterized by formula 5

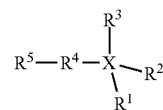

5 or pharmaceutically acceptable salts, solvates or prodrugs thereof. These compounds as provided in the context of the present invention are particularly useful as pharmaceuticals.

In formula 5, the groups $R^1$, $R^5$ and X have the same meanings and preferred meanings as described and defined herein above for the corresponding groups in formula 1, while the groups $R^2$, $R^3$ and $R^4$ in formula 5 have the following meanings:

Either (i) $R^2$ is a $C_{1-4}$ alkyl group, $R^3$ is —H or is absent, and $R^4$ is —CH$_2$—CH(—OH)—CH$_2$—;

or (ii) $R^2$ is a $C_{1-4}$ alkyl group, $R^3$ is —H, a $C_{1-4}$ alkyl group or is absent, and $R^4$ is a $C_{3-6}$ alkylene group which is substituted with one or more groups independently selected from —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH or —O(CH$_2$)$_3$OH;

or (iii) $R^2$ and $R^3$ are mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —O($C_{1-3}$ alkyl), —O—C(O)—($C_{1-3}$ alkyl), $C_{1-3}$ alkyl, —NH$_2$, —NH($C_{1-3}$ alkyl) or —N($C_{1-3}$ alkyl)($C_{1-3}$ alkyl), and $R^4$ is a $C_{3-6}$ alkylene group which is substituted with one or more groups independently selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH or —O(CH$_2$)$_3$OH.

In one preferred embodiment, $R^2$ in formula 5 is methyl, $R^3$ is —H or is absent, and $R^4$ is —$CH_2$—CH(—OH)—$CH_2$—.

In another further preferred embodiment, $R^2$ in formula 5 is methyl, $R^3$ is —H, a $C_{1-4}$ alkyl group (particularly methyl) or is absent, and $R^4$ is a $C_{3-6}$ alkylene group which is substituted with one or more groups independently selected from —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2$)$_2$OH or —O($CH_2$)$_3$OH. Said $C_{3-6}$ alkylene group may be linear or branched; preferably, the alkylene group is linear. The alkylene group has 3 to 6 (i.e., 3, 4, 5 or 6) carbon atoms, and preferably has 3 carbon atoms. The one or more groups with which the alkylene group is substituted is/are preferably selected independently from —O($C_{1-3}$ alkyl), —O—C(O)—($C_{1-3}$ alkyl), —O—C(O)—O($C_{1-3}$ alkyl), —O($CH_2$)$_2$OH, or —O($CH_2$)$_3$OH. More preferably, the one or more groups with which the alkylene group is substituted is/are selected independently from —O—C(O)—($C_{1-3}$ alkyl), —O($CH_2$)$_2$OH, or —O($CH_2$)$_3$OH. More preferably, $R^2$ is methyl, $R^3$ is —H, methyl or is absent, and $R^4$ is —($CH_2$)$_p$—CH(—$R^{41}$)—$CH_2$—, wherein the moiety —($CH_2$)$_p$— within the group —($CH_2$)$_p$—CH(—$R^{41}$)—$CH_2$— is connected to $R^5$, p is an integer from 1 to 4 (i.e., 1, 2, 3 or 4; preferably, p is 1), and $R^{41}$ is selected from —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2$)$_2$OH, or —O($CH_2$)$_3$OH, preferably from —O($C_{1-3}$ alkyl), —O—C(O)—($C_{1-3}$ alkyl), —O—C(O)—O($C_{1-3}$ alkyl), —O($CH_2$)$_2$OH, or —O($CH_2$)$_3$OH, and more preferably from —O—C(O)—($C_{1-3}$ alkyl), —O($CH_2$)$_2$OH, or —O($CH_2$)$_3$OH. Even more preferably, $R^2$ is methyl, $R^3$ is —H, methyl or is absent, and $R^4$ is —$CH_2$—CH(—$R^{41}$)—$CH_2$—, wherein $R^{41}$ is selected from —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2$)$_2$OH, or —O($CH_2$)$_3$OH, preferably from —O($C_{1-3}$ alkyl), —O—C(O)—($C_{1-3}$ alkyl), —O($CH_2$)$_2$OH, or —O($CH_2$)$_3$OH, and more preferably from —O—C(O)—($C_{1-3}$ alkyl) or —O($CH_2$)$_2$OH. Yet even more preferably, $R^2$ is methyl, $R^3$ is —H, methyl or is absent, and $R^4$ is —$CH_2$—CH(—O—C(O)—($C_{1-3}$ alkyl))—$CH_2$—. In the aforementioned embodiments of $R^2$, $R^3$ and $R^4$, it is particularly preferred that $R^3$ is methyl.

In another preferred embodiment, $R^2$ and $R^3$ in formula 5 are mutually linked to form a pyrrolidine ring, a piperidine ring or an azepane ring (preferably a piperidine ring) together with the nitrogen atom X to which they are attached, wherein the pyrrolidine ring, the piperidine ring or the azepane ring may be substituted with one or more (such as, e.g., one, two, three, or four), preferably one or two, more preferably one, groups independently selected from —OH, —O($C_{1-3}$ alkyl), —O—C(O)—($C_{1-3}$ alkyl), $C_{1-3}$ alkyl, —$NH_2$, —NH($C_{1-3}$ alkyl) or —N($C_{1-3}$ alkyl)($C_{1-3}$ alkyl); and $R^4$ is a $C_{3-6}$ alkylene group which is substituted with one or more (such as, e.g., one, two, three, or four) groups, preferably one or two groups, more preferably one group, independently selected from —OH, —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2$)$_2$OH, or —O($CH_2$)$_3$OH. Said $C_{3-6}$ alkylene group ($R^4$) may be linear or branched and preferably is linear. The alkylene group has 3 to 6 (i.e., 3, 4, 5 or 6) carbon atoms, and preferably has 3 carbon atoms. The one or more groups with which the alkylene group ($R^4$) is substituted is/are preferably selected independently from —OH, —O($C_{1-3}$ alkyl), —O—C(O)—($C_{1-3}$ alkyl), —O—C(O)—O($C_{1-3}$ alkyl), —O($CH_2$)$_2$OH, or —O($CH_2$)$_3$OH. More preferably, the one or more groups with which the alkylene group ($R^4$) is substituted is/are selected independently from —OH, —O—C(O)—($C_{1-3}$ alkyl), —O($CH_2$)$_2$OH, or —O($CH_2$)$_3$OH. It is furthermore preferred that said pyrrolidine ring, said piperidine ring or said azepane ring ($R^2$ and $R^3$) is unsubstituted or substituted with one group —OH. Accordingly, it is particularly preferred that $R^2$ and $R^3$ are mutually linked to form a piperidine ring together with the nitrogen atom X to which they are attached, wherein the piperidine ring is optionally substituted with one group —OH, preferably in para position with respect to the nitrogen atom X, and $R^4$ is —($CH_2$)$_p$—CH(—$R^{41}$)—$CH_2$—, wherein the moiety —($CH_2$)$_p$— within the group —(OH$_2$)$_p$—CH(—$R^{41}$)—$CH_2$— is connected to $R^5$, p is an integer from 1 to 4 (i.e., 1, 2, 3 or 4; preferably, p is 1), and $R^{41}$ is selected from —OH, —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2$)$_2$OH, or —O($CH_2$)$_3$OH, preferably from —OH, —O($C_{1-3}$ alkyl), —O—C(O)—($C_{1-3}$ alkyl), —O($CH_2$)$_2$OH, or —O($CH_2$)$_3$OH, and more preferably from —OH, —O—C(O)—($C_{1-3}$ alkyl), —O($CH_2$)$_2$OH, or —O($CH_2$)$_3$OH. More preferably, $R^2$ and $R^3$ are mutually linked to form a piperidine ring together with the nitrogen atom X to which they are attached, wherein the piperidine ring is optionally substituted with one group —OH (preferably in para position with respect to the nitrogen atom X), and $R^4$ is —$CH_2$—CH(—$R^{41}$)—$CH_2$—, wherein $R^{41}$ is selected from —OH, —O($C_{1-3}$ alkyl), —O—C(O)—($C_{1-3}$ alkyl), —O—C(O)—O($C_{1-3}$ alkyl), —O—C(O)—$NH_2$, —O—C(O)—NH($C_{1-3}$ alkyl), —O—C(O)—N($C_{1-3}$ alkyl)($C_{1-3}$ alkyl), —O($CH_2$)$_2$OH, or —O($CH_2$)$_3$OH, preferably from —OH, —O($C_{1-3}$ alkyl), —O—C(O)—($C_{1-3}$ alkyl), —O($CH_2$)$_2$OH, or —O($CH_2$)$_3$OH, and more preferably from —OH, —O—C(O)—($C_{1-3}$ alkyl) or —O($CH_2$)$_2$OH. Even more preferably, $R^2$ and $R^3$ are mutually linked to form a piperidine ring together with the nitrogen atom X to which they are attached, wherein the piperidine ring is optionally substituted with one group —OH (preferably in para position with respect to the nitrogen atom X), and $R^4$ is —$CH_2$—CH(—OH)—$CH_2$— or —$CH_2$—CH(—O—C(O)—($C_{1-3}$ alkyl))—$CH_2$—.

Preferred examples of the compound of formula 5 are the compounds 1a, 1b, 1c, 1d or 1e shown below or pharmaceutically acceptable salts, solvates or prodrugs thereof:

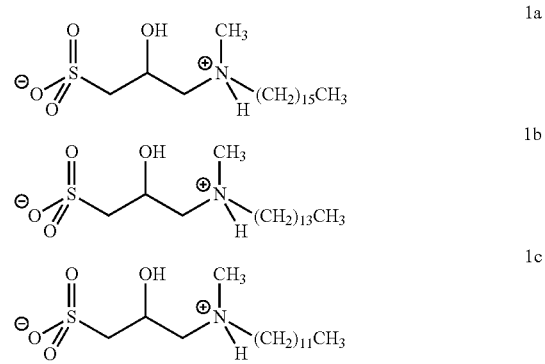

-continued

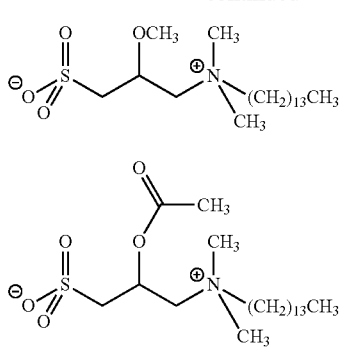

The compound of formula 5 may, in accordance with the above definition, also be a compound of the following formula 6

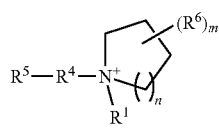

or a pharmaceutically acceptable salt, solvate or prodrug thereof.

The groups $R^1$ and $R^5$ in formula 6 have the same meanings and preferred meanings as defined herein above for the corresponding groups in formula 5.

In formula 6, n is 1, 2, or 3. Preferably, n is 2.

m is an integer from 0 to 4. Preferably, m is 0, 1, or 2; more preferably, m is 0 or 1; even more preferably, m is 1.

$R^4$ in formula 6 is a $C_{3-6}$ alkylene group which is substituted with one or more (such as, e.g., one, two, three, or four) groups, preferably one or two groups, more preferably one group, independently selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH. The alkylene group may be linear or branched; preferably, the alkylene group is linear. The alkylene group has 3 to 6 (i.e., 3, 4, 5 or 6) carbon atoms, and preferably has 3 carbon atoms. The one or more groups with which the alkylene group is substituted is/are preferably selected independently from —OH, —O($C_{1-3}$ alkyl), —O—C(O)—($C_{1-3}$ alkyl), —O—C(O)—O($C_{1-3}$ alkyl), —O(CH$_2$)$_2$OH, or —O(CH$_2$)$_3$OH. More preferably, the one or more groups with which the alkylene group is substituted is/are selected independently from —OH, —O—C(O)—($C_{1-3}$ alkyl), —O(CH$_2$)$_2$OH, or —O(CH$_2$)$_3$OH. It is particularly preferred that $R^4$ is —(CH$_2$)$_p$—CH(—R$^{41}$)—CH$_2$—, wherein the moiety —(CH$_2$)$_p$— within the group —(CH$_2$)$_p$—CH(—R$^{41}$)—CH$_2$— is connected to $R^5$, p is an integer from 1 to 4 (i.e., 1, 2, 3 or 4; preferably, p is 1), and $R^{41}$ is selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH, preferably from —OH, —O($C_{1-3}$ alkyl), —O—C(O)—($C_{1-3}$ alkyl), —O—C(O)—O($C_{1-3}$ alkyl), —O(CH$_2$)$_2$OH, or —O(CH$_2$)$_3$OH, and more preferably from —OH, —O—C(O)—($C_{1-3}$ alkyl), —O(CH$_2$)$_2$OH, or —O(CH$_2$)$_3$OH. Even more preferably, $R^4$ is —CH$_2$—CH(—R$^{41}$)—CH$_2$—, wherein $R^{41}$ is selected from —OH, —O($C_{1-3}$ alkyl), —O—C(O)—($C_{1-3}$ alkyl), —O—C(O)—O($C_{1-3}$ alkyl), —O—C(O)—NH$_2$, —O—C(O)—NH($C_{1-3}$ alkyl), —O—C(O)—N($C_{1-3}$ alkyl)($C_{1-3}$ alkyl), —O(CH$_2$)$_2$OH, or —O(CH$_2$)$_3$OH, preferably from —OH, —O($C_{1-3}$ alkyl), —O—C(O)—($C_{1-3}$ alkyl), —O(CH$_2$)$_2$OH, or —O(CH$_2$)$_3$OH, and more preferably from —OH, —O—C(O)—($C_{1-3}$ alkyl) or —O(CH$_2$)$_2$OH. Yet even more preferably, $R^4$ is —CH$_2$—OH(—OH)—CH$_2$— or —CH$_2$—CH(—O—C(O)—($C_{1-3}$ alkyl))—CH$_2$—.

Each $R^6$ in formula 6 is independently selected from —OH, —O($C_{1-3}$ alkyl), —O—C(O)—($C_{1-3}$ alkyl), $C_{1-3}$ alkyl, —NH$_2$, —NH($C_{1-3}$ alkyl) or —N($C_{1-3}$ alkyl)($C_{1-3}$ alkyl). Preferably, each $R^6$ is —OH.

It is to be understood that each $R^6$ is attached to a carbon atom of the pyrrolidine, piperidine or azepane ring. It is further to be understood that, if m is 0, the pyrrolidine, piperidine or azepane ring (to which $R^6$ would be attached) is unsubstituted, i.e. is substituted with hydrogen.

In one embodiment, n is 1 or 3, and m is 0.

In a preferred embodiment, n is 2, m is 1, and $R^6$ is —OH, —O($C_{1-3}$ alkyl), —O—C(O)—($C_{1-3}$ alkyl), $C_{1-3}$ alkyl, —NH$_2$, —NH($C_{1-3}$ alkyl) or —N($C_{1-3}$ alkyl)($C_{1-3}$ alkyl), in particular —OH. In this embodiment, it is further preferred that $R^6$ is in para position in respect of the ring nitrogen atom $N^+$.

In accordance with the disclosure of the present invention, the compounds of formulae 5 and 6 can be used as medicaments, particularly in the treatment, prevention or amelioration of an inflammatory, autoimmune and/or allergic disorder and also in the treatment, prevention or amelioration of a proliferative, neoplastic or dysplastic disease or disorder, including the specific disorders described and discussed herein above in connection with the compounds of formulae 3 and 4.

The compounds to be used in accordance with the present invention, in particular the compounds of formula 1, 2, 3, 4, 5 or 6, can be prepared by methods known in the field of synthetic chemistry.

For example, compounds of the general formula 1, 3 or 5 can be prepared by N-alkylation of N-alkylated alkylamines (or other N-alkylated hydrocarbylamines, such as, e.g., N-alkylated alkenylamines or N-alkylated alkynylamines) using appropriately hydroxysubstituted ω-chloro-1-alkanesulfonates under basic conditions. In a similar way, the related phosphonates or carboxylates are generated, e.g., by using appropriately hydroxysubstituted ω-chloro-1-alkanephosphonates or appropriately hydroxysubstituted w-chloro-1-alkanecarboxylates. The corresponding N,N-dialkylated quarternary ammonium derivatives can be obtained by standard N-alkylation using, e.g., alkyl iodides.

Compounds of the general formula 2, 4 or 6 can be prepared by consecutive N-alkylation of appropriately functionalised pyrrolidine, piperidine or azepane derivatives using the aforementioned appropriately hydroxysubstituted w-chloro-1-alkanesulfonates, -phosphonates or -carboxylates followed by alkyl iodides.

In addition to the unsubstituted hydroxyl derivatives of general formula 1 or 2 (i.e., compounds of formula 1 or 2 in which $R^4$ is an alkylene substituted with —OH), subsequent O-alkylation, O-acylation or O-carbamoylation using protocols employed in the literature provide the corresponding O-functionalised derivatives.

The compounds of formula 1, 2, 3, 4, 5 or 6 can also be prepared in analogy to the synthetic routes described in the examples section.

As used herein, the term "hydrocarbon group" refers to a group consisting of carbon atoms and hydrogen atoms, which group may be saturated or unsaturated, linear, branched or cyclic, aliphatic or aromatic. A "$C_{10\text{-}20}$ hydrocarbon group" denotes a hydrocarbon group having 10 to 20 carbon atoms.

As used herein, the term "alkyl group" refers to a monovalent saturated aliphatic (i.e. non-aromatic) acyclic hydrocarbon group, which may be linear or branched and does not comprise any carbon-to-carbon double bond or any carbon-to-carbon triple bond.

As used herein, the term "alkenyl group" refers to a monovalent unsaturated aliphatic acyclic hydrocarbon group, which may be linear or branched and comprises at least one carbon-to-carbon double bond while it does not comprise any carbon-to-carbon triple bond.

As used herein, the term "alkynyl group" refers to a monovalent unsaturated aliphatic acyclic hydrocarbon group, which may be linear or branched and comprises at least one carbon-to-carbon triple bond and optionally one or more carbon-to-carbon double bonds.

As used herein, the term "alkylene group" refers to a divalent saturated aliphatic (i.e. non-aromatic) acyclic hydrocarbon group which may be linear or branched and does not comprise any carbon-to-carbon double bond or any carbon-to-carbon triple bond.

The scope of the invention embraces all pharmaceutically acceptable salt forms of the compounds of formula 1, 2, 3, 4, 5 or 6, which may be formed, e.g., by protonation of an atom carrying an electron lone pair which is susceptible to a protonation, such as an amino group, with an inorganic or organic acid, or as a salt of a carboxylic acid group with a physiologically acceptable cation as they are well-known in the art. Exemplary base addition salts comprise, for example, alkali metal salts such as sodium or potassium salts; alkaline earth metal salts, such as calcium or magnesium salts; ammonium salts; aliphatic amine salts, such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts, such as pyridine salts, picoline salts, quinoline salts or isoquinoline salts; quaternary ammonium salts, such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts, such as arginine salts or lysine salts. Exemplary acid addition salts comprise, for example, mineral acid salts, such as hydrochloride, hydrobromide, hydroiodide, sulfate salts, nitrate salts, phosphate salts (such as phosphate, hydrogenphosphate or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts, such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts, such as aspartate or glutamate salts.

Moreover, the scope of the invention embraces solid forms of the compounds of formula 1, 2, 3, 4, 5 or 6 in any solvated form, including e.g. solvates with water, for example hydrates, or with organic solvents, such as, e.g., methanol, ethanol, isopropanol or acetonitrile, i.e. as a methanolate, ethanolate, isopropanolate or acetonitrilate, respectively; or in the form of any polymorph. The invention also embraces each one of the polymorphs of compound 1a described in Example 5.

Furthermore, the formulae in the present application are intended to cover all possible stereoisomers, including enantiomers and diastereomers, of the indicated compounds. Thus, all stereoisomers of the compounds of the present invention, in particular the compounds of formula 1, 2, 3, 4, 5 or 6, are contemplated as part of the present invention, either in admixture or in pure or substantially pure form. The scope of the compounds according to the invention embraces all the possible stereoisomers and their mixtures. It very particularly embraces the racemic forms and the isolated optical isomers. The racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization.

Pharmaceutically acceptable prodrugs of compounds of the present invention, in particular of the compounds of formula 1, 2, 3, 4, 5 or 6, are derivatives which have chemically or metabolically cleavable groups and become, by solvolysis or under physiological conditions, the compounds of the present invention which are pharmaceutically active in vivo. Prodrugs of compounds of the present invention may be formed in a conventional manner with a functional group of the compounds, such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound of the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. When a compound of the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. When a compound of the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

The compounds described herein may be administered as compounds per se in their use as pharmacophores or pharmaceutical compositions or may be formulated as medicaments. Within the scope of the present invention are pharmaceutical compositions comprising, as an active ingredient, a compound of formula 1, 2, 3, 4, 5 or 6 as defined above. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds according to the invention, in particular the compounds of formula 1, 2, 3, 4, 5 or 6, or the above described pharmaceutical compositions comprising one or more compounds of formula 1, 2, 3, 4, 5 or 6 may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients, such as microcrystalline cellulose, lactose, sodium citrate, calcium carbonate, dibasic calcium phosphate and glycine, disintegrants, such as starch (preferably corn, potato or tapioca starch), sodium starch glycolate, croscarmellose sodium and certain complex silicates, and granulation binders, such as polyvinylpyrrolidone, hydroxypropylmethylcellulose (HPMC), hydroxypropylcellulose (HPC), sucrose, gelatin and acacia. Additionally, lubricating agents, such as magnesium stearate, stearic acid, glyceryl behenate and talc may be included. Solid compositions of a similar type may also be employed as fillers in gelatin capsules. Preferred excipients in this regard include lactose, starch, a cellulose, milk suaar or high molecular weight polyethylene glycols. For aqueous suspensions and/or elixirs, the agent may be combined with various sweetening or flavoring agents, coloring matter or dyes, with emulsifying and/or suspending agents and with diluents, such as water, ethanol, propylene glycol and glycerin, and combinations thereof.

Alternatively, said compounds or pharmaceutical compositions can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative, such as a benzylalkonium chloride. Alternatively, they may be formulated in an ointment, such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of formula 1, 2, 3, 4, 5 or 6 for administration to a human (of approximately 70 kg body weight) may be 0.05 to 5000 mg, preferably 0.1 mg to 1000 mg, of the active ingredient per unit dose. The unit dose may be administered, for example, 1 to 4 times per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The compounds of the present invention, including the compounds of formula 1, 2, 3, 4, 5 or 6, may be administered in the context of a monotherapy or in cotherapy with one or more other pharmaceutical agents. For example, one compound of the present invention or two or more compounds of the invention may be used in combination with one or more immunomodulatory drugs and/or anti-inflammatory drugs for the treatment, prevention or amelioration of an inflammatory, autoimmune and/or allergic disorder.

A pharmaceutical composition may comprise said compound(s), immunomodulatory drug(s) and/or anti-inflammatory drug(s). Cotherapy may also include the administration of two or more compounds of the present invention in the absence of further immunomodulatory drugs or anti-inflammatory drugs. It is also envisaged herein that the compound(s), immunomodulatory drug(s) and/or anti-inflammatory drug(s) might be linked, for example, by formation of conjugates. Accordingly, the compounds, immunomodulatory drugs and/or anti-inflammatory drugs may be administered to a subject simultaneously. Also, a pharmaceutical composition may comprise only the compound(s) of the present invention, while the one or more immunomodulatory drugs and/or anti-inflammatory drugs are comprised in a different pharmaceutical composition. In that case, it may still be possible to administer the compound(s) of the invention, immunomodulatory drugs and/or anti-inflammatory drugs simultaneously; however, the compound(s) of the invention may also be administered before and/or after the one or more immunomodulatory drugs and/or anti-inflammatory drugs. It is readily apparent to a person skilled in the art how to administer, for example, one or more compounds of the present invention, one or more immunomodulatory drugs, and/or one or more anti-inflammatory drugs in cotherapy.

It is envisaged that one or more of the compounds as described herein, in particular the compounds of formula 1, 2, 3, 4, 5 or 6, may be used in combination with one or more immunomodulatory drugs and/or one or more anti-inflammatory drugs.

The one or more immunomodulatory drugs include, without being limited thereto: antimetabolites such as, e.g., azathioprine, mycophenolic acid, leflunomide, teriflunomide, or methotrexate; macrolides such as, e.g., tacrolimus, ciclosporin, or pimecrolimus; IL-2 inhibitors such as, e.g., abetimus or gusperimus; TNF-α inhibitors such as, e.g., thalidomide or lenalidomide; IL-1 receptor antagonists such as, e.g., anakinra; mammalian target of rapamycin (mTOR) proteins such as, e.g., sirolimus, deforolimus, everolimus, temsirolimus, zotarolimus, or biolimus A9; monoclonal antibodies such as, e.g., eculizumab, infliximab, adalimumab, certolizumab pegol, afelimomab, golimumab, Mepolizumab, omalizumab, nerelimomab, faralimomab, elsilimomab, lebrikizumab, ustekinumab, muromonab-CD3, otelixizumab, teplizumab, visilizumab, clenoliximab, keliximab, zanolimumab, efalizumab, erlizumab, afutuzumab, ocrelizumab, pascolizumab, lumiliximab, teneliximab, toralizumab, aselizumab, galiximab, gavilimomab, ruplizumab, belimumab, ipilimumab, tremelimumab, bertilimumab, lerdelimumab, metelimumab, natalizumab, tocilizumab, odulimomab, basiliximab, daclizumab, inolimomab, zolimomab aritox, atorolimumab, cedelizumab, dorlixizumab, fontolizumab, gantenerumab, gomiliximab, maslimomab, morolimumab, pexelizumab, reslizumab, rovelizumab, siplizumab, talizumab, telimomab aritox, vapaliximab, or vepalimomab; polyclonal antibodies such as, e.g., anti-thymocyte globulin or anti-lymphocyte globulin; or fusion proteins such as, e.g., abatacept, belatacept, etanercept, pegsunercept, aflibercept, alefacept, or rilonacept.

Furthermore, the one or more anti-inflammatory drugs include, without being limited thereto: pyrazolidine or butylpyrazolidine derivatives such as, e.g., ampyrone, clofezone, kebuzone, metamizole, mofebutazone, oxyphenbutazone, phenazone, phenylbutazone, sulfinpyrazone, or feprazone; acetic acid derivatives such as, e.g., aceclofenac, acemetacin, alclofenac, bromfenac, bumadizone, bufexamac, diclofenac, difenpiramide, etodolac, fentiazac, indometacin, ketorolac, lonazolac, oxametacin, proglumetacin, sulindac, tolmetin, zomepirac, or amfenac; oxicam derivatives such as, e.g., ampiroxicam, droxicam, lornoxicam, meloxicam, piroxicam, or tenoxicam; propionic acid derivatives such as, e.g., alminoprofen, benoxaprofen, dexibuprofen, dexketoprofen, fenbufen, fenoprofen, flunoxaprofen, flurbiprofen, ibuprofen, ibuproxam, indoprofen, ketoprofen, naproxen, oxaprozin, pirprofen, suprofen, or tiaprofenic acid; fenamic acid derivatives such as, e.g., flufenamic acid, meclofenamic acid, mefenamic acid, tolfenamic acid, niflumic acid, morniflumate, or azapropazone; COX-2 inhibitors such as, e.g., celecoxib, etoricoxib, lumiracoxib, parecoxib, rofecoxib, or valdecoxib; or nabumetone, glucosamine, benzydamine, glycosaminoglycan, magnesium salicylate, proquazone, superoxide dismutase/orgotein, nimesulide, diacerein, tenidap, oxaceprol, or chondroitin sulfate.

Cotherapy using the compound(s) of the present invention, immunomodulatory drug(s) and/or anti-inflammatory drug(s) may result in a synergistic effect, i.e. the agents acting together may create an effect greater than that predicted by knowing only the separate effects of the individual agents. Such a synergistic effect might be particularly advantageous if less amounts of the compound(s), immunomodulatory drug(s) and/or anti-inflammatory drug(s) may then be used. Thus, possible side-effects of the compound(s), immunomodulatory drug(s) and/or anti-inflammatory drug(s) might be diminished or avoided.

It is furthermore particularly envisaged that one or more of the compounds of the invention, in particular the compounds of formula 1, 2, 3, 4, 5 or 6, may be used in combination with one or more immunomodulatory drugs as described herein above and/or one or more anti-inflammatory drugs as described herein above (including, for example, azathioprine, ciclosporin, D-penicillamine, gold salts, hydroxychloroquine, leflunomide, methotrexate, minocycline, sulfasalazine, or cyclophosphamide) for the treatment, prevention or amelioration of rheumatoid arthritis.

The term "treatment of a disorder or disease" as used herein, such as "treatment of an inflammatory, autoimmune and/or allergic disorder", is well known in the art. "Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

"Treatment of a disorder or disease" may, for example, lead to a halt in the progression of the disorder or disease (e.g., no deterioration of symptoms) or a delay in the progression of the disorder or disease (in case the halt in progression is of a transient nature only). "Treatment of a disorder or disease" may also lead to a partial response (e.g., amelioration of symptoms) or complete response (e.g., disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to healing of the disorder or disease) and palliative treatment (including symptomatic relief).

Also the term "prevention of a disorder or disease" as used herein, such as "prevention of an inflammatory, autoimmune and/or allergic disorder", is well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

The subject or patient, such as the subject in need of treatment, prevention or amelioration, may be a eukaryote, an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orangutan, gibbon), or a human. The meaning of the terms "eukaryote", "animal", "mammal", etc. is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, rabbits, fruit flies like *Drosophila melagonaster* and nematodes like *Caenorhabditis elegans*. Non-limiting examples of agronomically important animals are sheep, cattle and pig, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig; and in particular a canine, such as a dog); even more preferably, the subject/patient is a human.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: Inhibition of mast cell degranulation by compounds 1a (FIG. 1A), 1b (FIG. 1B), 1c (FIG. 1C), 1d (FIG. 1D), 1e (FIG. 1E) and miltefosine (FIG. 1F). Dose-response curves for inhibition of 8-hexosaminidase release from RBL-2H3 cells stimulated with antigen-specific IgE and triggered with antigen are shown (means±standard error of the mean).

Figure 2:
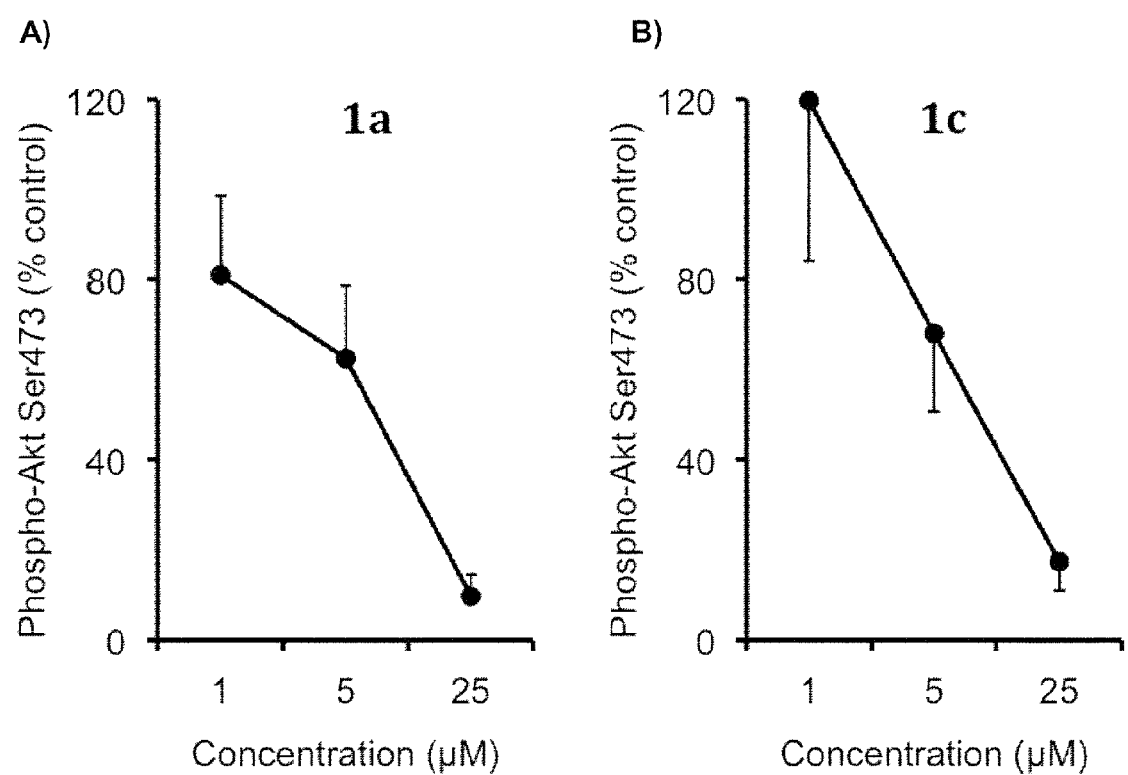

FIG. 2: Inhibition of Akt phosphorylation on Ser473 by compounds 1a (FIG. 2A) and 1c (FIG. 2B). Percentage of total Akt phosphorylated on Ser473 is expressed as a percentage of control untreated cells induced with IgE and antigen for 15 min (shown are means±standard deviation).

Figure 3:
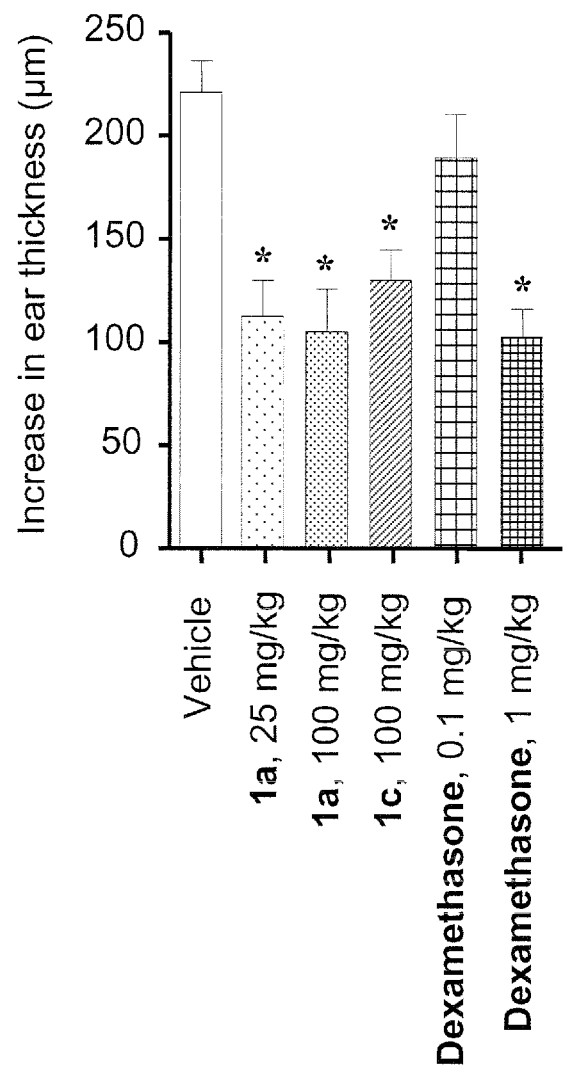

FIG. 3: Effect of compounds 1a and 1c and dexamethasone on mouse ear swelling in the DTH response in mice (data are means±standard deviations of 8 mice; * $p<0.01$ vs. vehicle control (Dunnett's post hoc test)).

Figure 4:
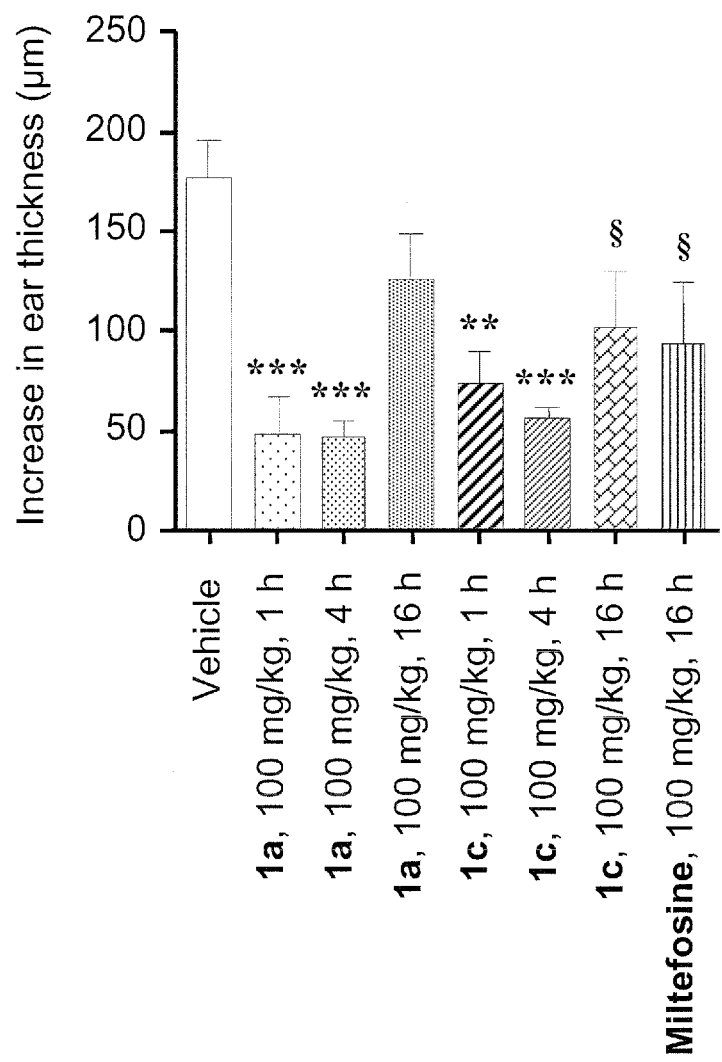
Figure 4:
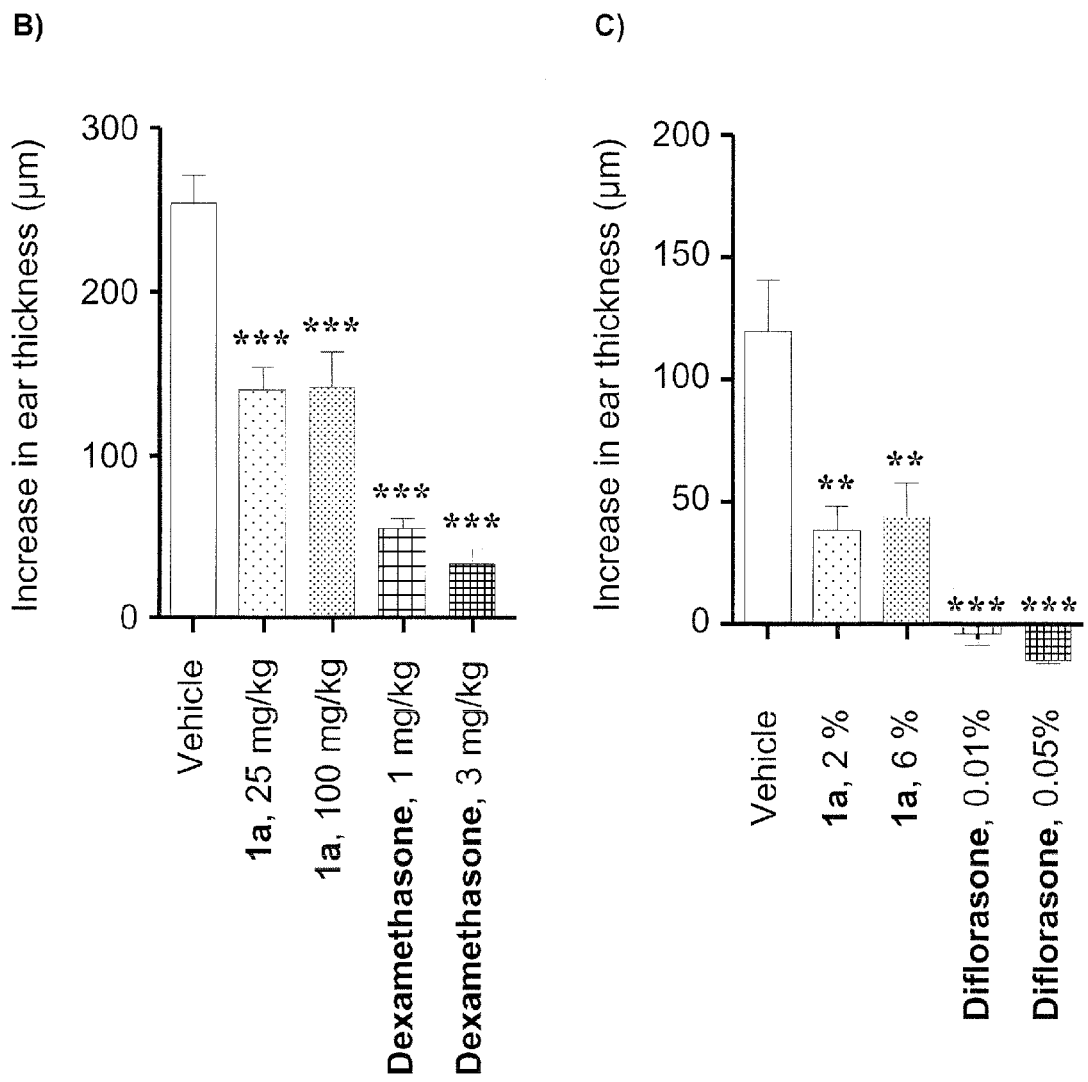
Figure 4:
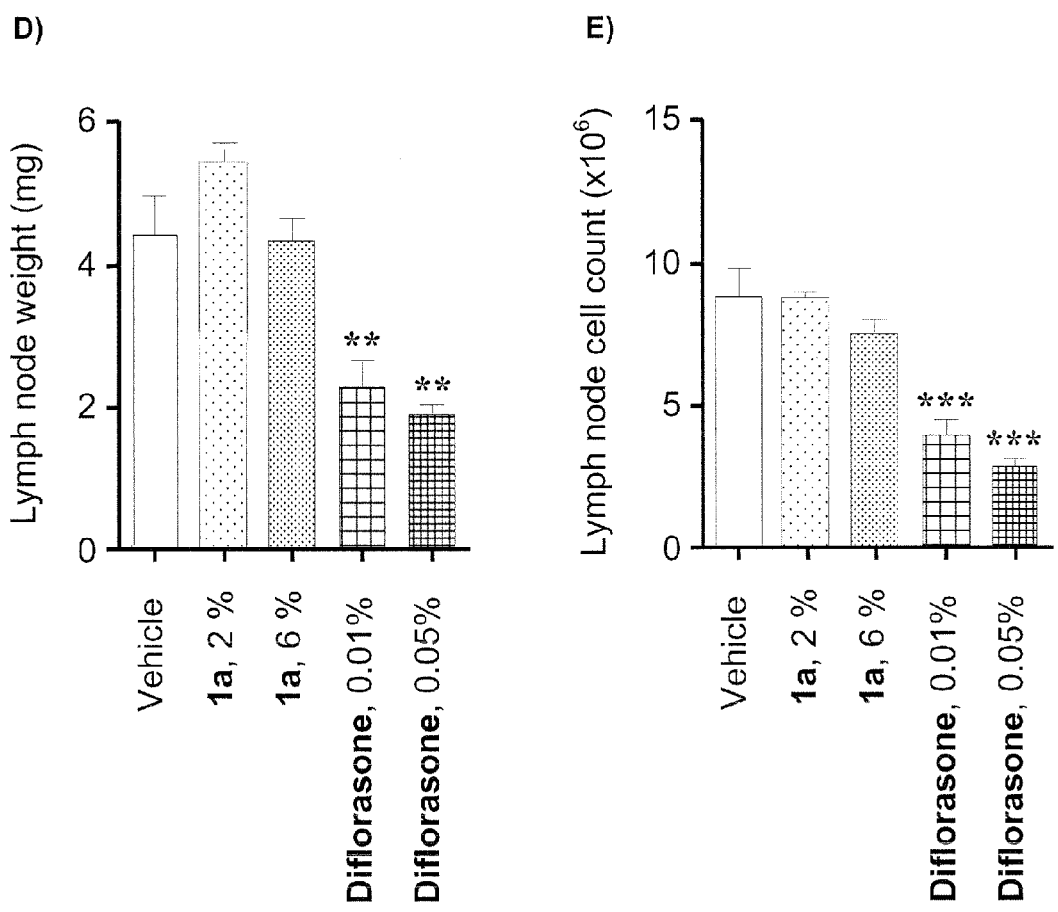

FIG. 4: Effect of compounds 1a and 1c on mouse ear swelling in the allergic contact dermatitis model in mice. FIG. 4A shows a comparison of the inhibitory activity of compounds 1a and 1c and miltefosine at different administration times before antigen challenge (data are means±SEM of 7 mice;  $p<0.01$, * $p<0.001$ vs. vehicle control (Dunnett's post hoc test), §$p<0.05$ vs. vehicle control (t-test)). FIGS. 4B and 4C show a comparison of the inhibitory activity of compound 1a and corticosteroids after systemic (oral) application (FIG. 4B) or topical application (FIG. 4C) (data are means±SEM of 7 mice;  $p<0.01$, * $p<0.001$ vs. vehicle control (Dunnett's post hoc test)). FIGS. 4D and 4E show the local lymph node reaction, comparing the effect of compound 1a and topical diflorasone on local lymph node weight (FIG. 4D) and cell number (FIG. 4E) (data are means±SEM of 7 mice;  $p<0.01$, * $p<0.001$ vs. vehicle control (Dunnett's post hoc test)).

Figure 5:
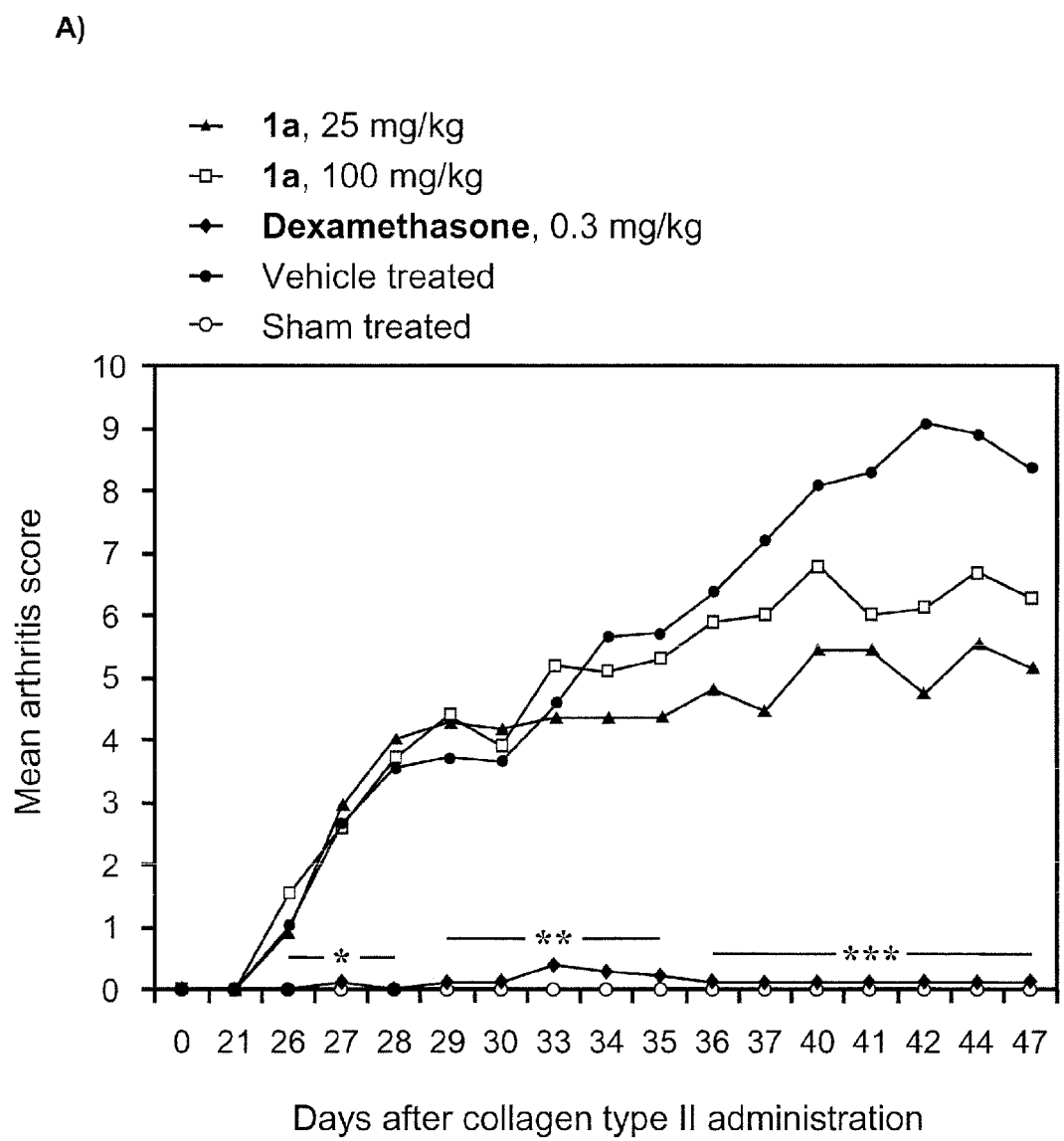
Figure 5:
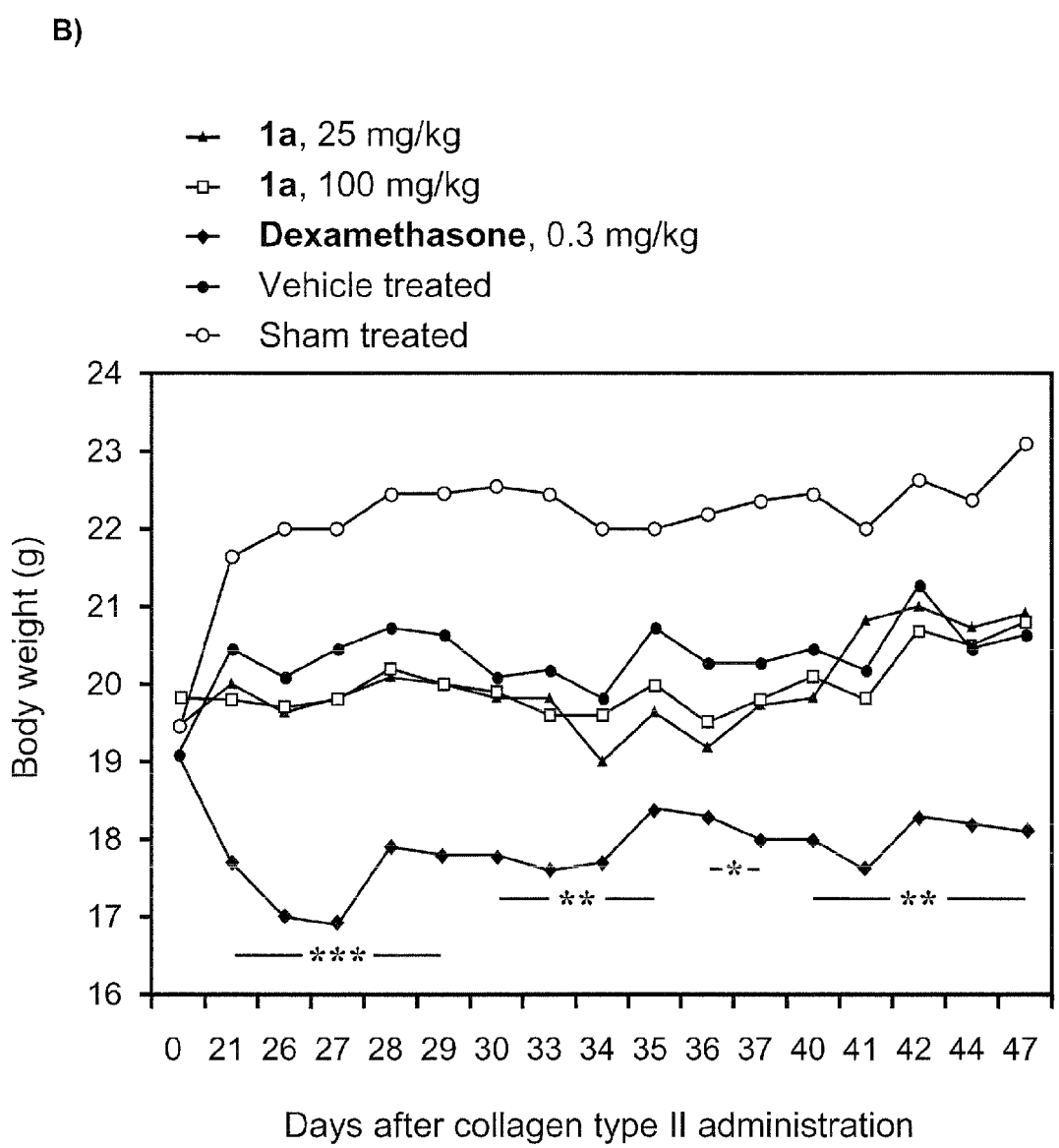
Figure 5:
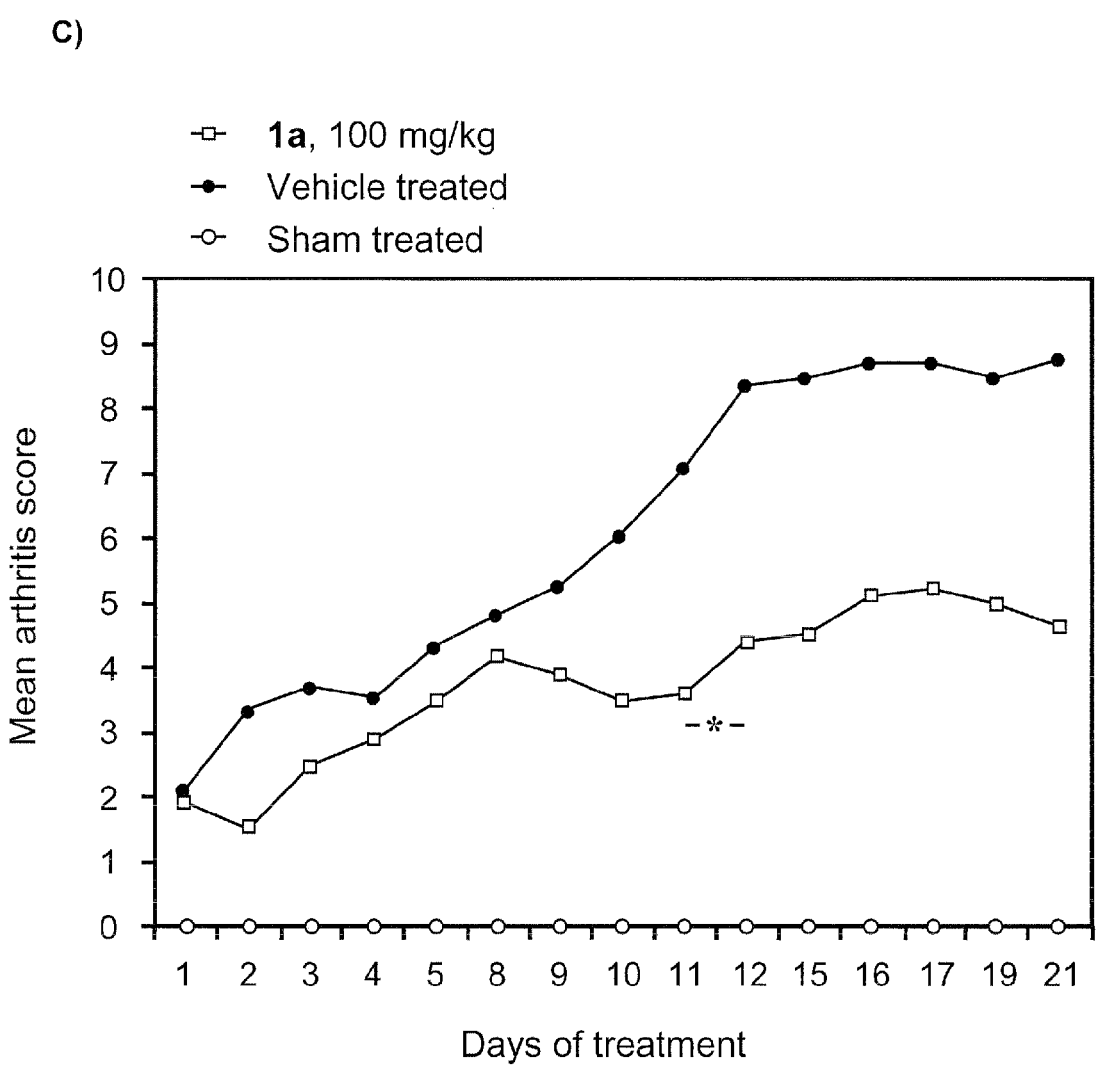
Figure 5:
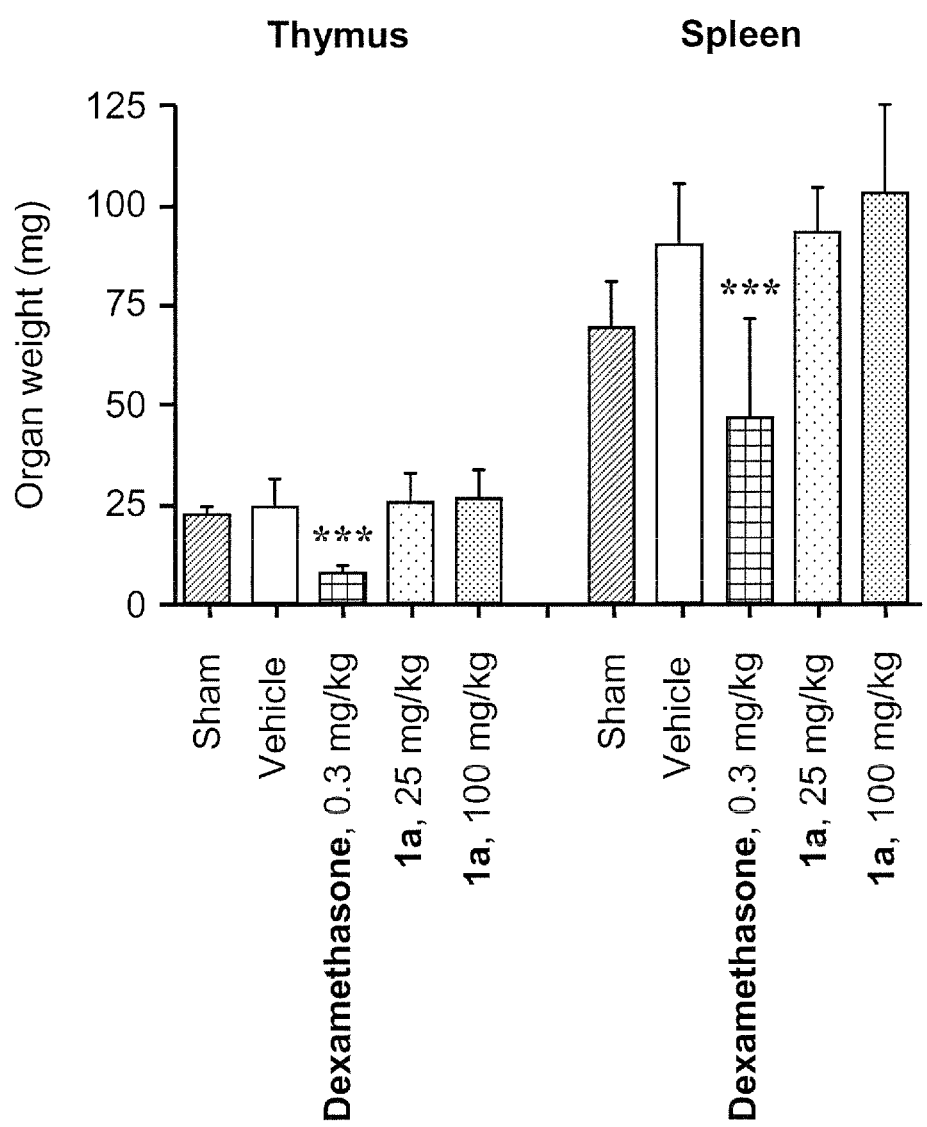

FIG. 5: Effect of compound 1a on collagen type II-induced arthritis (CIA) in mice. FIG. 5A shows the effects on arthritis score during the course of type II CIA of compound 1a and dexamethasone using a prophylactic regimen (data are means of 10-11 mice; * $p<0.02$,  $p<0.01$, * $p<0.001$ vs. vehicle control (t-test)). FIG. 5B shows the effects on body weight changes during the course of type II CIA of compound 1a and dexamethasone using a prophylactic regimen (data are means of 10-11 mice; * $p<0.02$,  $p<0.01$, * $p<0.001$ vs. vehicle control (t-test)). FIG. 5C shows the effects on arthritis score during the course of type II CIA of compound 1a using a therapeutic regimen (data are means of 11 mice; * $p<0.02$ vs. vehicle control (t-test)). FIG. 5D shows the effects on spleen and thymus weight during the course of type II CIA of compound 1a and dexamethasone using a prophylactic regimen (data are means of 10-11 mice; *** $p<0.001$ vs. vehicle control (t-test)).

Figure 6:
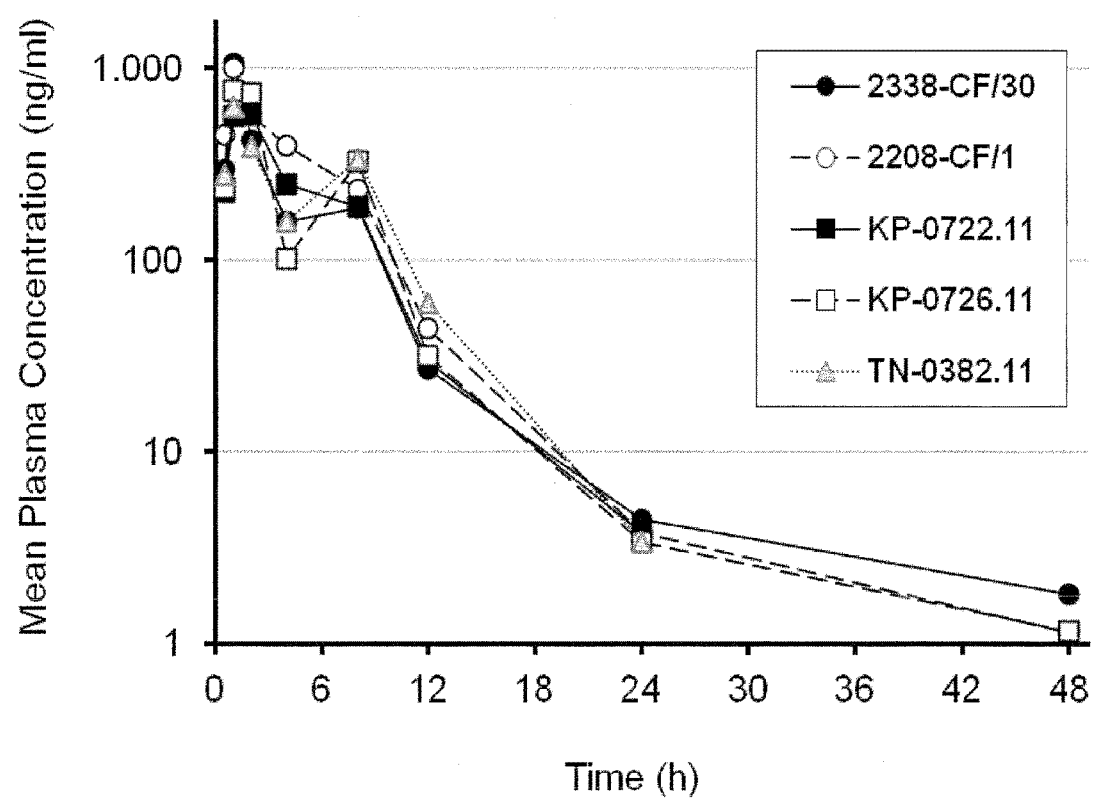

FIG. 6: Mean plasma concentration-time profiles (semi-logarithmic) of five polymorphic forms of compound 1a in female Balb/c mice (n=3) following a single oral administration of 100 mg/kg in 0.5% methylcellulose solution.

The invention will now be described by reference to the following examples which are merely illustrative and are not to be construed as a limitation of the scope of the present invention.

EXAMPLES

Example 1: Preparation of 2-hydroxy-3-(N-methylhexadecylammonio)propane-sulfonate 1a, 2-hydroxy-3-(N-methyltetradecylammonio)propanesulfonate 1b and 2-hydroxy-3-(N-methyldodecylammonio)propanesulfonate 1c Sodium-3-chloro-2-hydroxy-1-propanesulfonate (3.83 g, 19.5 mmol), N-methyldodecylamine (3 g, 15 mmol) and N,N-diisopropylethylamine (DIEA) (2.5 g, 19.5 mmol) are suspended in 20 mL of dry dimethylformamide (DMF) and heated to 130° C. under argon atmosphere for 24 h. The volatiles are removed under reduced pressure and the residue is chromatographed on silica using dichloromethane/methanol using a stepwise increase of eluent strength from 9:1 to 4:1. Compound 1c is obtained as white material (4.61 g, 91%).

MS (ESI): 338.2 (M+H$^+$), 675.5 (2M+H$^+$), 697.5 (2M+Na$^+$).

$^1$H-NMR (300 MHz, CDCl$_3$): δ=0.81 (t, J=6.9, 3H), 1.1-1.35 (m, 18H), 1.68 (m, 2H), 2.89 (d/d, J=4.5/13.1, 3H), 2.95-3.45 (m, 6H), 4.52 (m, 1H), 8.90 (br. s, 1H), 9.17 (br. s, 1H).

Compounds 1a and 1b are prepared in a similar way using N-methylhexadecylamine (for 1a) or N-methyitetradecylamine (for 1b) instead of N-methyldodecylamine.

Examples 2 and 3: Preparation of 2-methoxy-3-(N,N-dimethyl-N-tetradecylammonio)-propane-1-sulfonate 1d and 2-acetoxy-3-(N,N-dimethyltetradecylammonio)propanesulfonate 1e Compound 1b (440 mg, 1.2 mmol), methyl iodide (1.36 g, 9.6 mMol) and K$_2$CO$_3$ (497 mg, 3.6 mmol) are suspended in a mixture of acetone (10 mL) and dichloromethane (2 mL). The mixture is stirred at room temperature overnight. The volatiles are removed under reduced pressure and the residue is purified by preparative HPLC to yield 287 mg of 2-hydroxy-3-(N,N-dimethyl-N-tetradecylammonio)propane-1-sulfonate as a white solid.

For the preparation of compound 1d sodium hydride (12 mg, 0.52 mmol) is suspended in dry THF (2 mL) under argon atmosphere. The aforementioned 2-hydroxy-3-(N,N-dimethyl-N-tetradecylammonio)propane-1-sulfonate (65 mg, 0.17 mmol) is dissolved in a mixture of DMF (1 mL) and THF (1 mL) and added dropwise. Methyl iodide (111 mg, 0.78 mmol) is added and the mixture is stirred at room temperature for 4 d. The mixture is quenched with 0.5 mL of methanol, the solvent is removed under reduced pressure and the residue is purified by preparative HPLC to yield 57 mg (85%) of 1d as white material.

MS (ESI): 394.4 (M+H$^+$), 787.7 (2M+H$^+$).

$^1$H-NMR (300 MHz, CDCl$_3$): δ=0.81 (t, J=6.9, 3H), 1.1-1.35 (m, 22H), 1.70 (m, 2H), 2.80 (m, 1H), 3.13 (s, 6H), 3.2-3.45 (m, 4H), 3.33 (s, 3H), 4.18 (m, 2H).

For the preparation of compound 1e the aforementioned 2-hydroxy-3-(N,N-dimethyl-N-tetradecylammonio)propane-1-sulfonate (140 mg, 0.37 mmol) and 4-dimethylaminopyridine (DMAP) (3.4 mg, 0.028 mmol) are dissolved in dichloromethane (5 mL) under argon atmosphere. Acetic anhydride (32 mg, 0.31 mmol) and DIEA (40 mg, 0.31 mmol) are added and the mixture is stirred at room temperature for 24 h. The volatiles are removed under reduced pressure and the residue is purified by preparative HPLC to give 123 mg (79%) of 1e as a solid material.

MS (ESI): 422.3 (M+H$^+$), 843.6 (2M+H$^+$).

$^1$H-NMR (300 MHz, CDCl$_3$): δ=0.81 (t, J=6.9, 3H), 1.1-1.35 (m, 22H), 1.69 (m, 2H), 2.02 (s, 3H), 3.14 (d, J=5.5, 6H), 3.0-3.3 (m, 4H), 3.69 (m, 1H), 4.30 (d/m, J=14.4, 1H), 5.64 (m, 1H).

Example 4: Large Scale Synthesis of Compound 1a

N-methyl hexadecanamide

A suspension of 1775 g of palmitic acid (6.92 mol) and 12.5 L of toluene was stirred at 20-25° C. and 1245 g (1.5 eq., 10.38 mol) thionyl-chloride added. The reaction mixture was heated under reflux for 12 h, then cooled to 20-25° C. and evaporated to dryness on a rotary evaporator under vacuum (bath temperature, 70° C.). The yield of crude palmitoyl chloride was 2475 g.

The crude palmitoyl chloride was dissolved in 5.0 L of dichloromethane (DCM), cooled to 0-5° C. and 3.5 L of methylamine (5. 7 eq., 39.44 mol) in 5.8 L of dichloromethane was added dropwise over a period of 105 minutes (maintaining the temperature at 5-10° C.). The suspension was allowed to warm to 20-25° C. and stirred overnight and the mixture then evaporated to dryness on a rotary evaporator under vacuum (bath temperature, 40° C.). The residue was suspended in 3.1 L of deionized water and the product collected by filtration. The filter cake was washed with 3.0 L of deionized water and 0.5 L of methylcyclohexane and then dried to a constant weight in vacuo at 55° C. The yield was 96.0% (1790 g) of a beige powder; GC: 99.3 area %, water content: 0.07%.

Hexadecyl(methyl)amine

To a mixture of 15.75 kg of tetrahydrofuran (THF) and 2.76 kg (1.3 eq., 8.64 mol) lithium aluminium hydride (solution in THF), was added 1.79 kg (6.64 mol) of the N-methyl hexadecanamide in portions, at 20-25° C. (gas evolution). The reaction mixture (a yellowish-brown suspension) was stirred at reflux for 3 h. The reaction mixture was cooled to 5-10° C. and quenched by dropwise addition of 360 ml of deionized water, 360 ml of 20% sodium hydroxide solution and 1.04 L of deionized water. Tonsil (Süd-Chemie), 370 g, was added to the reaction mixture and the resulting suspension filtered and the filter cake washed with 2.08 kg of THF. The filtrate was evaporated to dryness on a rotary evaporator under vacuum (bath temperature, 60° C.). The yield was 88.0% (1495 g) of an off-white powder; GC: 98.2 area %. The material was stored under nitrogen.

2-hydroxy-3-(N-methylhexadecylammonio)propanesulfonate, sodium/potassium salt (compound 1a)

Batch 1:
Hexadecyl(methyl)amine (814 g, 3.18 mol) was suspended in 10.7 L of dimethylformamide (DMF). The off-white suspension was stirred at 20-25° C. and 847.5 g (1.3 eq., 4.13 mol) of sodium 3-chloro-2-hydroxypropane sulfonate hemihydrate, 573 g (1.3 eq., 4.13 mol) of potassium carbonate and 99.4 g (0.2 eq., 0.63 mol) of sodium iodide were added. The mixture was stirred at 50-60° C. for 69 h under nitrogen. HPLC showed 25.1 area % of product in the reaction mixture. DMF was removed by vacuum distillation (bath temperature, 80° C.) and the residue suspended in 4.95 L of THF and evaporated to 1.3 kg of celite. Soxhlet extraction with 20.0 L of THF:methanol (9:1) was carried out for 4.5 days. The extract was evaporated to dryness to leave a residue, which was confirmed by HPLC to be mostly side-products and which was discarded. The celite was removed from the Soxhlet extractor and dried to constant weight at 60° C. in vacuo. (3220 g). The celite was suspended in 32.0 L of methanol and heated to reflux. The mixture was filtered hot and the filtrate crystallized at 0-5° C., yielding 1016 g of yellowish powder (HPLC: 96.6 area %) of compound 1a as the sodium/potassium salt.

Batch 2:

Hexadecyl(methyl)amine (480.8 g, 1.88 mol) was suspended in 6.25 L of DMF. The off-white suspension was stirred at 20-25° C. and 500 g (1.3 eq., 2.44 mol) of sodium 3-chloro-2-hydroxypropane sulfonate hemihydrate, 338.4 g (1.3 eq., 2.44 mol) of potassium carbonate and 58.6 g (0.2 eq., 0.37 mol) of sodium iodide were added. The mixture was stirred at 50-60° C. for 82 h under nitrogen. HPLC showed 30.5 area % of product in the reaction mixture. DMF was removed by vacuum distillation (bath temperature, 80° C.) and the residue crystallized from 12.35 L of boiling methanol. The mixture was filtered hot (insoluble part: 226.0 g) and the filtrate was crystallized at 0-5° C., yielding 562.0 g of yellowish powder, (HPLC: 97. 6 area %) of compound 1a as the sodium/potassium salt.

2-hydroxy-3-(N-methylhexadecylammonio)propane-sulfonate (compound 1a)

The sodium/potassium salt, 1100 g, obtained as described above, were suspended in 11 L of chloroform:methanol (4:1). The pH was adjusted to 5 with saturated HCl solution in 2-propanol (the amount of HCl was determined by titration of a sample). Filtration and evaporation to dryness yielded 990 g of brownish-yellow, amorphous solid (HPLC: 96.8 area %). Crystallization of this solid, as described above, from 8.0 L of methanol yields 715.0 g of compound 1a (HPLC: 98.6 area %).

Material of this grade was further purified by repeated crystallization from boiling methanol, with removal of insolubles by hot filtration if required. Recrystallization from isopropanol:water (4:1) may also be used. In a typical experiment, 805 g of compound 1a were dissolved in 2.4 L of isopropanol:water (4:1) at reflux, slowly cooled to 0-5° C., filtered and dried to yield 730 g (90% recovery) of compound 1a as an off-white powder (HPLC: 98.8 area %). In order to obtain a uniform polymorph, recrystallization from methanol under anhydrous conditions is preferred for the final crystallization step.

Purification is continued until the following criteria are met:

Purity by HPLC: >99 area %
Residue on ignition: <0.8%
Conductivity of 1% aqueous suspension: <50 µS/cm
NMR, MS: Conform with structure.
Elemental analysis: consistent with composition.

Example 5: Polymorphism of Compound 1a

Compound 1a can be crystallized from a variety of solvents. From a practical standpoint (ease of filtration, low toxicity of solvent), methanol, ethanol and isopropanol are preferred. Addition of 5-25% water to water-miscible solvents increases solubility and leads to a steeper temperature coefficient of solubility, reducing the amount of solvent required. Less preferred solvents for recrystallization are 1-propanol, n-butanol, acetone, acetonitrile, THF and ethyl acetate. Recrystallization from water is hard to control and frequently leads to difficulties in filtration.

Starting from dry crude material and solvent, compound 1a is obtained as an anhydrate. Pure monohydrate can be obtained by crystallization from water. In a typical procedure, 150 g of compound 1a (anhydrate) was dissolved in 2 L of deionized boiling water, then seeded with compound 1a hydrate and the mixture was allowed to slowly cool to room temperature (RT). The precipitate was collected by filtration and dried at 35° C., 15 mbar, yielding 134.6 g (86% recovery) of an off-white solid. Karl Fischer titration and elementary analysis indicated the presence of a monohydrate.

NMR indicates that compound 1a monohydrate remains associated with water even in solution, leading to an unexpectedly complex pattern of signals. Reversible coalescence is observed upon heating. This water-associated form is likely to be present under physiological conditions. The anhydrate shows the expected, simpler NMR spectrum.

Compound 1a monohydrate (batch 2338-CF/30): 1H-NMR (600 MHz, CDCl3): δ=0.87 (t, 3H), [1.15-1.35 (m), 1.31 (br. s), Σ=26H], 1.74 (br. s, 2H), [2.93 (d, J=4.5), 2.98 (d, J=4.7), 2.95-3.35 (m), 3.44 (br. d, J=12.7), Σ=12H], 4.58 (br. s, 1H), 9.21 (br. s, 0.5H), 9.48 (br. s, 0.5H).

Compound is anhydrate (batch 2208-CF/1): 1H-NMR (500 MHz, CDCl3): δ=0.86 (t, 3H), [1.15-1.35 (m), 1.30 (br. s), Σ=26H], 1.73 (br. s, 2H), 2.94 (s, 3H), [3.05-3.25 (m), 3.12 (d, J=5.7), Σ=5H], 3.39 (br. d, J=12.1, 1H), 4.58 (br. d, J=6.1, 1H). (δ>5 ppm: no signals.)

Both the monohydrate from water and the anhydrate from methanol form thin, micrometer-sized platelets of irregular shape. X-ray powder diffraction (XRPD) indicates a layered structure with a base period of 27 A for both forms. Both forms can be easily interconverted. According to differential scanning calorimetry (DSC) analysis, the monohydrate loses its water between 60° C. and 90° C. The anhydrate can be converted to monohydrate by exposure to air of 100% relative humidity for 4 days. Only one equivalent of water is taken up and the consistency of the material remains unchanged.

Crystallization from mixtures of water and water-miscible solvents yielded the anhydrate in most cases. In one experiment with methanol containing 10-25% water, formation of monohydrate was observed, but was poorly reproducible. Due to the more predictable outcome, anhydrous conditions are preferred for the final steps of purification.

A pseudo-polymorph can be characterized by crystallizing compound 1a from methanol and analyzing the wet material by XRPD. In the methanol-wet sample, a layered structure is observed in which the base period is 28.5 Å. During drying at ambient temperature, both 27 Å (anhydrate) and 28.5 Å are observed together. Upon complete drying at ambient temperature, only the diffraction pattern of the anhydrate is observed. Thus, this crystallization proceeds through the intermediate stage of an instable methanol solvate in which methanol is weakly intercalated between the layers of the anhydrate structure.

In total, four different polymorphs could be identified by XRPD (Table 1). Upon heating, clear solutions could be obtained with water, methanol, ethanol, isopropanol and the solvent:water (9:1) mixtures. Polymorphs from other solvents were obtained by equilibration of suspensions of form A in the respective solvents.

TABLE 1

Polymorphs of compound 1a obtained from various solvents.

| Solvent system | Water of crystallization | Batch number | Crystal form* |
|---|---|---|---|
| Water; methanol; acetonitrile:water (1:1); acetone:water (1:1); ethanol:water (1:1) | | n/a | A |
| Solvent:water (9:1); solvents tested were methanol, ethanol, isopropanol, THF | | n/a | A |
| Water | Monohydrate | KP-0722.11 | A |
| Methanol | Anhydrate | KP-0726.11 | A |
| Methanol; partial sodium salt | Anhydrate (alkaline) | TN-0382.11 | A |
| Methanol:water (1:1) | Monohydrate | 2338-CF/30 | A |
| Methanol, traces of sodium salt | Anhydrate | 2208-CF/1 | A |
| Ethanol; n-butanol; ethylacetate; THF | | n/a | B |
| Acetonitrile | | n/a | C |
| Isopropanol | | n/a | D |

*Arbitrary nomenclature

Crystal forms A-C are relatively similar and share the same base period of 27 Å. While form A shows two broad reflexions at about 4.0 and 4.4 Å, form B shows a single sharp reflexion at about 4.5 Å. Form C shows the same sharp 4.5 Å reflexion as form B, plus a complex pattern of four more medium broad reflexions between 3.6 and 4.4 Å.

Surprisingly, crystallization from neat isopropanol yields a highly crystalline polymorph which is very different from all other samples in Table 1. In form D, the base period is reduced to 22.8 Å and it does not share any major reflexion with form A. Unlike form A from methanol, this form does not change during drying. Crystallizing from isopropanol containing 10% of water is enough to yield form A instead.

This demonstrates that methanol is to be preferred for the final steps of crystallization, because it yields a uniform lattice type (form A), even in the presence of small amounts of water. Ease of removal and ease of filtration are also best for methanol. Of form A, both the anhydrate and the monohydrate (which can be prepared by hydration of anhydrate) are suitable for pharmaceutical use. The monohydrate of form A is advantageous in that it will not take up further water during stress-testing in stability tests (such as, e.g., open incubation at 40° C./80% humidity for 3 to 6 months). Accordingly, the use of the monohydrate of form A may be preferred in terms of storage stability.

The present invention embraces all polymorphs of the compounds disclosed herein, including the above-described polymorphs of compound 1a.

Example 6: Inhibition of Mast Cell Degranulation

Introduction

Mast cells are key effector cells involved in allergic and inflammatory diseases, and the Rat Basophilic Leukemia clone 2H3 (RBL-2H3) cell line is a commonly used model of allergen dependent immune modulator release (degranulation) in mast cells. On their surface, they express the high affinity receptor for IgE (FcεRI). Upon binding of antigen-specific IgE to the receptor, cells become sensitized to the IgE specific antigen (allergen). When IgE-sensitized cells then encounter multivalent antigen, the antigen clusters IgE-FcεRI complexes and initiates a signal transduction cascade that leads to degranulation, that is, the release of inflammatory mediators, such as cytokines, eicosanoids, histamine and enzymes. The assay can be used as a screening method to identify immune-modulating compounds, in particular compounds useful in the medical management of allergic and inflammatory diseases and asthma. β-hexosaminidase was previously shown to be released with the same kinetics as histamine (Schwartz et al., J Immunology; 123:1445-1450 (1979)), thus offering a simple means to monitor degranulation. The RBL-2H3 cell line has been successfully used to identify compounds with anti-allergic activity (Choo et al. Planta Med., 69:518-522 (2003)).

Materials and Methods

Materials

Chemicals: Rat anti-DNP IgE monoclonal antibody was acquired from Biozol (BZL06936), dinitrophenyl-conjugated human serum albumin (A6661) and Triton X-100 (T9284) were from Sigma-Aldrich, 4-methylumbelliferyl-N-acetyl-β-D-glucosaminide (474502), Phorbol-12-myristate-13-acetate (524400) and thapsigargin (586005) from Calbiochem. Ionomycin (ALX-450-006) was purchased from Alexis Biochemicals. DMSO was from Merck (1.02950.0500) or Sigma-Aldrich (D2650). Cell culture media and supplements, Minimum Essential Medium (21090-022), Minimum Essential Medium without Phenol Red (51200-046), RPMI 1640 Medium (31870-025), L-Glutamine (25030-024) and 0.05% Trypsin-EDTA (25300-054), were obtained from Invitrogen. Fetal bovine serum (A15-151) was from PAA Laboratories. Other reagents were standard laboratory grade or better.

Buffers and solutions: Phosphate buffered saline (PBS) and 1 M HEPES were provided by the in-house service facility. Tyrodeis buffer (TyB) consisted of Minimum Essential Medium without Phenol Red supplemented with 2 mM L-glutamine and 20 mM HEPES. Lysis buffer consisted of 25 mM Tris-HCl, pH 7.5, 150 mM NaCl, 5 mM EDTA and 0.1% (w/v) Triton X-100. DNP-HSA was dissolved to 1 mg/ml in water. MUG substrate solution consisted of 2.5 mM 4-methylumbelliferyl-N-acetyl-β-D-glucosaminide in 0.05 M citrate, pH 4.5; stop solution was 0.1 M $NaHCO_3$/0.1 M $Na_2CO_3$, pH 10.

Consumables and equipment: For small-volume liquid handling procedures, Rainin LTS electronic pipettes were routinely used (Mettler-Toledo). Costar-Corning 24-well plates (3337) were centrifuged in an Eppendorf 5804 R centrifuge. A Heraeus B15 table top incubator was used for incubations at 37° C. under non-sterile conditions. Fluorescence was measured in black Nunc 96-well plates (237105) using a microplate reader (Tecan Safire) or FlexStation 3 (Molecular Devices) multi-mode plate reader. Cells were maintained in Hera Cell 240 $CO_2$ incubators (Thermo Scientific). Serological pipettes (4487, 4488 and 4489) and cell culture flasks (431080) were from Corning-Costar, 1.5 and 2 ml microcentrifuge tubes (0030 120.086 and 0030 120.094) were from Eppendorf.

Cell Culture: RBL-2H3 cells obtained from the German Collection of Microorganisms and Cell Cultures (ACC312) (Braunschweig, Germany) were maintained in 70% Minimum Essential Medium with Earle's Salts, 20% RPMI 1640 Medium, 10% FBS and 2 mM L-glutamine in 95% air/5% $CO_2$ at 37° C. and routinely checked for mycoplasma contamination. Cells were passaged every 3-4 days; after washing cells once with 35 ml PBS cells were incubated 8 min with 5 ml 0.05% Trypsin-EDTA solution at 37° C. Cells were removed from the incubator, 15 ml culture medium was added and cells were resuspended by repeated pipetting.

Cell seeding: cells were harvested with Trypsin-EDTA as described and 50-100 μl cell suspension seeded into Costar CellBind 24 well cluster plates (no. 3337). Plates were kept for 30 min at RT under the sterile hood before being transferred to the incubator. Cells were used within one or two days after seeding.

Measurement of β-Hexosaminidase Release

Experimental Procedures

For sensitization, cells for immediate use were sensitized 6-12 h after plating; cells to be used the following day were sensitized 26-38 h after plating. Culture plates were removed from the incubator and checked for cell growth and contamination. The medium was discarded and cells were sensitized with anti-DNP IgE (0.4 µg/ml) in 0.4 ml culture medium overnight. Following overnight sensitization, cells were washed with 0.8 ml pre-warmed TyB and 0.38 ml test compound or vehicle control (supplemented or not with 1% FBS) were added to duplicate wells. Samples were adjusted to contain 1% vehicle for test compounds dissolved in organic solvents. Cells were incubated for 1 h at 37° C. At the end of the incubation period, cells were routinely stimulated with 20 µl DNP-HSA (2 µg/ml; final concentration 0.1 µg/ml) diluted in TyB and cells were incubated for 15 min at 37° C. Alternatively, cells were stimulated with 20 µl 5 µM ionomycin (final concentration 0.25 µM) or 20 µl 5 µM thapsigargin (final concentration 0.25 µM), both in the absence or presence of 20 nM PMA (final concentration).

Plates were removed from the incubator and immediately centrifuged at 4° C. for 5 min at 250×g and transferred to an ice bath. Aliquots of supernatants, 25 µl, were transferred to 96-well plates. Remaining supernatant was aspirated from control wells and cells were lysed in 400 µl lysis buffer for 5 min at RT on an orbital shaker at 450 rpm under non-sterile conditions. After lysis, 25 µl aliquots of lysates were transferred to 96-well plates.

MUG substrate solution, 100 µl, were added to supernatant and lysate samples and plates were incubated 30 min at 37° C. The reaction was terminated by addition of 150 µl stop solution. Fluorescence was measured at 365 nm excitation and 440 nm emission wavelengths.

Test compound preparation: test compounds were prepared in 1.5 or 2 ml microcentrifuge tubes and incubated for 30 min at 37° C. in a Thermomixer Comfort with agitation (750 rpm). An electronic multichannel pipette was used for rapid transfer of compound dilutions from microcentrifuge tubes to the cells.

Controls: controls used are defined as follows: negative control, supernatant of unstimulated cells was measured for unspecific β-hexosaminidase release; positive control, supernatant of DNP-HSA stimulated cells was measured for specific, antigen-stimulated (β-hexosaminidase release; maximum control, lysate of unstimulated cells was measured for total β-hexosaminidase content.

Assessment of Pharmacologic Effect

Degranulation (β-hexosaminidase release): Degranulation was calculated as the percentage of β-hexosaminidase released with respect to maximum control (total β-hexosaminidase) after subtraction of negative control (unspecific release) using the formula;

% Degranulation=100×(test compound−negative control)/(maximum control−negative control).

Inhibition of degranulation (inhibition of β-hexosaminidase release): Inhibition of degranulation was calculated as percent reduction of β-hexosaminidase release with respect to positive control (antigen-stimulated release) after subtraction of negative control (unspecific release) using the formula;

% Inhibition=100×(1(test compound−negative control)/(positive control−negative control)).

Measurement of Maximum Tolerated Concentration

The maximum tolerated concentration (MTC), i.e. the highest concentration of test compound that does not cause cytotoxicity, as determined by the release of lactate dehydrogenase, was measured over the tested concentration range. A commercially available cytotoxicity test was used (Promega Cytotox-One cat. #67891).

The safety index (SI) of a test compound is the ratio between the maximum tolerated concentration and the IC50 and is used as a measure of the relative safety of the test compound.

Results

Concentration-dependent inhibition of degranulation was determined for all test compounds over a concentration range, as shown in FIG. 1, and IC50 values (concentration at which 50% of maximal inhibition is reached) were determined for each compound together with the MTC values over the same concentration range (Table 2). Results are taken from at least three independent experiments.

TABLE 2

Inhibition of degranulation: IC50, MTC and SI values

| Compound | IC50 (µM) | MTC (µM) | SI |
|---|---|---|---|
| 1a | 6.9 | 75 | 10.9 |
| 1b | 5.1 | 100 | 19.6 |
| 1c | 4.1 | 200 | 48.8 |
| 1d | 3.3 | 75 | 22.7 |
| 1e | 3.9 | 100 | 25.6 |
| Miltefosine | 4.2 | 25 | 6.0 |

The MTC of the test compounds was 11-50 fold higher than their respective IC50s and hence, the inhibition of degranulation can be ascribed to a pharmacological effect and not to an effect secondary to cytotoxicity.

All substances outlined in Table 2 show IC50 values in the low micromolar range combined with high MTC values when compared to Miltefosine. Thus, the compounds according to the invention and, in particular compounds 1a to 1e, have an advantageously low cytotoxicity.

Mast cell degranulation is a key cellular event in allergic and inflammatory reactions, in particular in pathological events involving the release of mediators such as histamine, leukotrienes and prostaglandins as well as proteases. As consequence, the inhibition of mast cell degranulation is a valuable strategy for prevention or treatment of pathological processes involving the aforementioned mediators. Furthermore, the mast cell degranulation assay provides an estimate of the activity of test compounds in other cells that play a key role in the inflammatory response, such as granulocytes, macrophages and thymocytes, which release proinflammatory cytokines and chemokines and tissue eroding proteases.

Example 7: Inhibition of Activation of Akt Kinase

Introduction

The mast cell degranulation assay using the RBL-2H3 cell line (see example 6) was also used to determine the status of the PI3K/Akt axis. Activation of PI3K leads to production of PIP3 on the cytosolic side of the lipid bilayer. Akt is recruited to the PIP3 domain and subsequently activated by phosphorylation on residues Ser473 and Thr308. (Franke et al., Cell 81:727-736, (1995)). Once recruited to the membrane, it is phosphorylated and activated by other kinases (Hemmings, Science 275:628-630 (1997); Hemmings, Science 276:534 (1997); Downward, Science 279:673-674

(1998); Alessi et al., EMBO J. 15:6541-6551 (1996)). Western blotting of the phosphorylated Ser473 residue on Akt (phospho-Akt Ser473) is widely used to assess the level of activation of the PI3K/Akt axis.

Materials and Methods

Materials

All buffers and solutions used for the phosphor-Akt Ser473 assay were from Meso Scale Discovery. Tris Lysis Buffer consisted of 150 mM NaCl, 20 mM Tris, pH 7.5, 1 mM EDTA, 1 mM EGTA and 1% Triton-X-100. Complete Tris Lysis Buffer was prepared prior to use by addition of protease inhibitor, phosphatase inhibitors and PMSF. The 10× Tris Wash Buffer consisted of 500 mM Tris, pH 7.5, 1.5 M NaCl and 0.2% Tween-20. Blocker A was made up of bovine serum albumin in Tris Wash Buffer. Read Buffer T was used according to manufacturer's instructions. The Whole Cell Lysate Kits used were phospho-Akt Ser473 (K11100D, Lot K0011749) and total ERK1/2 (K11107D, Lot K0011698) as a loading control.

Equipment 12-well multichannel pipettes (30-300 µl) from Eppendorf were used. Assay plates were agitated on a TiMix 5 control (Edmund Buhler). Electrochemiluminescence detection was performed on a SECTOR Imager 6000 (Meso Scale Discovery).

Measurement of Phospho-Akt Ser473

Experimental Procedures

Protein assay: protein concentration was determined using the BCA (bicinchoninic acid) Protein Assay kit according to the manufacturer's instructions. Briefly, duplicate 10 µl samples of bovine serum albumin (BSA) standards, blank and lysates were incubated in a 96-well plate with 0.2 ml working reagent for 30 min at 37° C. Plates were cooled to room temperature for 5 min and absorbance at 562 nm was measured in a multi-mode plate reader. Protein concentrations were calculated using FlexStation 3 software (SoftMax Pro version 5.3). Protein concentration of lysates was determined from a standard curve (BSA) using a linear curve fit.

Phosphoprotein assay: protein phosphorylation was determined using the MULTI-SPOT® Assay System (Meso Scale Discovery), providing simultaneous detection of phosphorylated and total proteins. Briefly, capture antibodies against phosphorylated and total protein are patterned on distinct spots in the same well of 96-well plates. Sandwich immunoassay and electrochemiluminescence detection technology are combined to measure intensity of the emitted light from phosphorylated and total protein spots. Analysis of phosphor-Akt Ser473 was performed according to the manufacturer's instructions. The optimal amount of protein was determined at 5 µg lysate per well for ERK1/2 and 10 µg/well for phospho-Akt Ser473. Plates were blocked with 25 µl/well Blocker A for 1 h at room temperature with gentle agitation. During this time, the lysates were thawed and diluted to the desired protein concentration in complete Tris Lysis Buffer. Plates were washed four times in Tris Wash Buffer and 25 µl lysate per well added. Plates were incubated for 1-3 h at room temperature with agitation according to the manufacturer's recommendations. Plates were washed four times with Tris Wash Buffer, followed by addition of 25 µl/well of the respective detection antibody and incubation for 1 h at room temperature, with agitation. After a final four washes with Tris Wash Buffer 150 µl/well, Read Buffer T was added and plates read on a SECTOR Imager 6000 plate reader.

Assessment of Effects of Phospho-Akt Ser473

The mean background signal from each plate was subtracted from averaged raw data. The amount of total protein phosphorylated was expressed as % phosphoprotein according to the manufacturer's (Meso Scale Discovery) instructions.

Results

Levels of phospho-Akt Ser473 were determined in IgE sensitized and antigen stimulated cells after treatment without (positive control) or with 1, 5 and 25 µM test compound and normalized to levels of total Akt. Concentration-dependent inhibition of Akt phosphorylation on Ser473 was demonstrated, as shown in FIG. 2. Table 3 shows levels of normalized phospho-Akt Ser473 as a percentage of those in the positive control.

TABLE 3

Inhibition of Akt phosphorylation on Ser473 by compounds 1a and 1c

| Compound | Level of phospho-Akt Ser473 (% positive control) | | |
|---|---|---|---|
| | 1 µM | 5 µM | 25 µM |
| 1a | 80.8 ± 17.9 | 62.4 ± 16.1 | 9.7 ± 4.9 |
| 1c | 119.7 ± 35.7 | 67.9 ± 17.3 | 17.4 ± 6.4 |

Percentage of total Akt phosphorylated on Ser473 expressed as percentage of control untreated cells, after induction with IgE and antigen for 15 min.

A dose-dependent decrease in levels of phospho-Akt Ser473 was observed after treatment with all compounds outlined in Table 3. Thus, the compounds according to the invention can be used to reduce levels of activated Akt and, accordingly, are useful in the medical intervention in indications in which hyperactivated Akt plays a pathogenic role, such as inflammatory and allergic diseases, hyperproliferative diseases and other indications.

Example 8: Inhibition of the Delayed-Type Hypersensitivity (DTH) Reaction in Mice Introduction The anti-inflammatory and anti-allergic effects of compounds 1a and 1c were assessed in a mouse model of skin delayed-type hypersensitivity (DTH) reactions and compared to a vehicle control and to the reference drug dexamethasone. DTH reactions are antigen-specific cell-mediated immune responses, driven primarily by T helper type 1 (Th1) cells, similar to the tuberculin immunization response. The immune reaction induced by an ovalbumin challenge to animals previously sensitized with ovalbumin in Complete Freund's Adjuvant, is characterized by swelling (edema) at the site of challenge, e.g. the mouse ear. Dexamethasone, an anti-inflammatory steroid, reduces cell-mediated immune responses and was employed to validate the responsiveness of the assay to pharmacological treatment.

Materials and Methods

Materials

Ovalbumin (fraction V, lyophilized powder), complete Freud's adjuvant (CFA) and methylcellulose were obtained from Sigma-Aldrich, dexamethasone from Pharmaceutical Works Polfa (Pabianice, Poland).

Animals

Female BALB/cJW mice were bred at the University of Lodz, Lodz, Poland and housed in groups of 8 in makrolon cages with a 12 h light-dark cycle. Mice were given free access to food (Agropol S.j., Motycz, Poland) and water.

Antigen Sensitization and Challenge

Group size was n=8 mice unless otherwise stated. Test compounds were freshly prepared before administration.

Sensitization: The protein antigen, ovalbumin, was reconstituted in PBS at 4 mg/ml. An ovalbumin-CFA emulsion was prepared by mixing the protein solution with the CFA suspension at a ratio of 1:1, using two Luer-lock syringes. The emulsion was tested by putting a drop of emulsion onto PBS; if the emulsion remained as a tight droplet on the PBS, the emulsion was deemed ready. Mice were sensitized by subcutaneously injecting 25 μL of emulsion into each side of the tail (100 μg ovalbumin per mouse).

Challenge: On the sixth day after sensitization, DTH was elicited by challenging animals subcutaneously (gauge 30 needle, B. Braun Melsungen, Melsungen, Germany) in the left ears with 10 μL of a 1% suspension of heat-aggregated ovalbumin (HOVA) (100 μg ovalbumin per mouse). The right ears were administered subcutaneously with PBS and served to determine the individual differences in ear thicknesses. HOVA was prepared by heating a 5% solution of ovalbumin in saline for 1 h at 80° C. with occasional swirling. After cooling to room temperature and centrifugation (400 g, 10 min at 4° C.), the pellet was washed twice with saline, resuspended at 2% in PBS and aliquots stored at −30° C. Before injection, HOVA was diluted with an equal volume of PBS and sonicated. Ear thickness was measured with a precise spring-loaded caliper (Art. No. 7309, Mitutoyo, Kawasaki, Japan) before challenge, and 24 h after challenge.

Sensitization, challenge and ear thickness measurement were performed under anesthesia (ketamine 80 mg/kg plus xylazine 8 mg/kg, intraperitoneally).

Compound Administration

The anti-inflammatory effects of compounds 1a and 1c were compared to a vehicle control (0.5% methyl cellulose solution) and to the reference drug, dexamethasone. Test compounds were given at 25 or 100 mg/kg orally by gavage (Art. No. 432093, Harvard Apparatus GmbH, March-Hugstetten, Germany) 16 h and 3 h before sensitization and then twice daily with the final dose given 3 h prior to ear challenge (a total of 14 administrations). Dexamethasone was given at 0.1 or 1 mg/kg orally by gavage 3 h before sensitization and once daily with the final dose given 3 h prior to antigen challenge (a total of 7 administrations). All administrations were given in a volume of 10 mL/kg.

Quantification of Assay Results

To account for individual variability, the increase in right ear thickness, before and 24 h after administration of PBS, was subtracted from the HOVA-induced increase in left ear thickness. The increase in ear thickness was calculated by the difference between ear thickness before and 24 h after antigen challenge. Percent inhibition of ear swelling was calculated according to the following formula:

$$\% \text{ inhibition} = 100 \times (\text{IET}_{vehicle} - \text{IET}_{compound})/\text{IET}_{vehicle}$$

where $\text{IET} = (\text{ET}_{24\ hrs\ pc} - \text{ET}_{predose})_{HOVA\text{-treated ears}} - (\text{ET}_{24\ hrs\ pc} - \text{ET}_{predose})_{PBS\text{-treated ears}}$ (IET, increase ear thickness; ET, ear thickness; pc, post challenge)

Statistical Evaluation

Mean and standard deviation (SD) were calculated from individual ear edema values. Statistical evaluation was a one-way analysis of variance (ANOVA) with Dunnett's post hoc test or Student's t-test where appropriate.

Results

Suppression of mouse ear swelling by compounds 1a and 1c as well as dexamethasone, compared to vehicle control is shown in FIG. 3. Table 4 summarizes the inhibition of DTH for compounds 1a and 1c.

TABLE 4

Inhibition of mouse ear swelling by compounds 1a and 1c in the DTH response in mice.

| Compound | Inhibition of mouse ear swelling |
|---|---|
| 1a, 25 mg/kg | 49* |
| 1a, 100 mg/kg | 52* |
| 1c, 100 mg/kg | 41* |
| Dexamethasone, 0.1 mg/kg | 14 |
| Dexamethasone, 1.0 mg/kg | 53* |

*$p < 0.01$ vs. vehicle control (Dunnett's post hoc test)

Dexamethasone administered orally at a dose of 1 mg/kg, once daily over the whole sensitization period resulted in a significantly reduced DTH response, with inhibition of 53%. Such high dosing (overdose) is, however, not suitable for treatment of humans due to severe side effects of the corticosteroid and was only used to validate the responsiveness of the model. In addition, in the course of the current study, a significant loss in body weight of 9% ($p<0.01$ vs. vehicle control with the paired Student's t-test) was seen in the high dose dexamethasone group. A more clinically representative dose of dexamethasone in the mouse is 0.1 mg/kg, but at this dose inhibition was very low (14%) and did not reach significance indicating that only steroid doses which result in significant body weight loss upon repeated administration are active in this model.

Compound 1a, administered orally twice daily over the whole sensitization period at two dosing regimens, 25 mg/kg or 100 mg/kg, reduced the DTH response by 49% and 52%, respectively. The higher dose administration of compound 1c reduced DTH response by 41%. Hence, these compounds were able to produce an inhibition almost equivalent to that of the high dose of dexamethasone (up to 98% for 1a and 77% for 1c). In contrast to dexamethasone, no significant toxic side-effects of compounds 1a or 1c were observed during the course of the study.

The reduction of DTH response obtained by treatment with compounds 1a and 1c demonstrates that the compounds according to the invention and, in particular compounds 1a and 1c, are effective in the pharmaceutical intervention in allergic and inflammatory diseases involving antigen-specific cell-mediated immune responses. Even at the low dose, compound 1a provided for the same high inhibition of the DTH response as obtained by an overdose of dexamethasone, and thus represents a particularly preferred compound of the present invention.

Example 9: Inhibition of the Allergic Contact Dermatitis Inflammatory Response in Mice Introduction The anti-inflammatory and anti-allergic effects of compounds 1a and 1c were assessed in a mouse model of allergic contact dermatitis, a response driven primarily by T helper type 2 (Th2) cells. It has been demonstrated that BALB/c mice are susceptible to the allergen toluene-2,4-diisocyanate (TOD), producing an inflammatory condition of the skin with similar aspects to that of human atopic dermatitis (Baumer et al., J Pharm Pharmacol, 55:1107-1114 (2003); Baumer et al., Br J Dermatol. 151:823-830 (2004); Ehinger et al., Eur Pharmacol. 392:93-99 (2000)). In this model, an allergic dermatitis response is obtained by sensitizing mice to TDI and subsequently challenging them with antigen by topical administration onto the ears. A quantitative assessment of anti-inflammatory and anti-allergic effects of topically or orally administered test compounds is possible by measuring the resulting ear swelling. The advantages of the allergic contact dermatitis model (Zllner et al., Bioessays 26:693-6 (2004)) are reproducibility and reliability (>90% of BALB/c mice respond to sensitization), a short induction protocol, quantitative assessment by measuring ear thickness, atopic dermatitis-like skin lesions can be induced, and clinically relevant pharmaceuticals, such as corticosteroids, calcineurin-inhibitors and PDE4-inhibitors, are effective in this model.

Materials and Methods

Materials

Dexamethasone dihydrogenphosphate (Dexa-Inject) was obtained from Mibe GmbH, Jena, Germany and diflorasone diacetate from Basotherm, Biberach an der Diss, Germany.

Animals

Female BALB/c-mice were obtained from Charles River (Sulzfeld, Germany) at age 8 weeks. All animals were housed in groups of eight per cage at 22° C. with a 12 h light/dark-cycle. Water and a standard diet (Altromin, Lage/ Lippe, Germany) were available ad libitum. All animals were acclimatized for one week before experimental procedures were commenced.

TDI Sensitization, Allergen Challenge and Mouse Ear Swelling Test

Experimental procedures for BALB/c mice housing, TDI sensitization and challenge, and measurement of ear thickness were performed as previously described (Baumer et al., J Pharm Pharmacol. 55:1107-1114 (2003)) with the following modifications. For active sensitization, 100 µL of 5% (w/v) TDI was administered to the shaved and stripped abdominal epidermis on day one, and for the next three consecutive days, 50 µL of 5% (w/v) TDI was applied. The allergic reaction was boosted 21 days later by application of 50 µL of 0.5% (w/v) TDI. For the examination of test compound effects, the left ears were used for the TDI challenge (20 µL of 0.5% in acetone) and ear thickness measured 3 h before and 24 h after challenge.

Compound Administration for Systemic Treatment

Group size was n=7 mice unless otherwise stated. Test compounds were freshly prepared before administration.

Administration time: to determine optimal time for administration treatment groups were treated orally by gavage with 100 mg/kg of compound 1a or 1c (suspended in 0.5% tylose, 10 mL/kg) 1, 4 or 16 h before topical TDI challenge. One group was treated with 100 mg/kg miltefosine orally, 16 h before challenge (based on available data for optimal administration time for miltefosine) and vehicle treated mice received tylose (10 mL/kg) orally, 4 h before challenge.

Dose-response: two groups of mice were treated orally with compound 1a at 25 mg/kg or 100 mg/kg suspended in 0.5 tylose, 4 h before topical TDI challenge. Vehicle treated mice received 0.5% tyiose orally 4 h before challenge. As a positive control, dexamethasone was administered in saline solution at 1 mg/kg or 3 mg/kg, 2 h and 30 min before challenge and 1 h after challenge. The dose and dosing scheme for dexamethasone was based on previous experience showing a maximal effect in this model.

Compound Administration for Topical Treatment

Compound 1a was administered to two groups of mice topically in 20 µl of a 2% or 6% solution in propyleneglycol. The suspension was heated to 60° C. and mixed using a thermomixer (Eppendorf) until it became clear. The solution was applied, 2 h before topical TDI challenge by administration of 10 µl onto each of the inner and outer surfaces of the left ears. A vehicle group (n=5) was treated with propyleneglycol. As a positive control, diflorasone diacetate was administered at 0.01% (low dose) and 0.05% (high dose) in 20 µl acetone, 2 h before challenge. A basal control group was left untreated.

Determination of Local Lymph Node Weight and Cell Count

Directly after sacrifice, the ear draining lymph node (*Ln. auricularis*) was prepared and excised. Organ weight was determined by means of an analytical balance (Kern, Balingen, Germany). Single cell suspensions were prepared by means of a glass potter (VWR, Darmstadt, Germany) and cells were counted with a hemocytometer (Neubauer, VWR, Germany).

Statistical Evaluation

Mean and standard error of the mean (SEM) were calculated from individual ear edema values. Statistical evaluation was a one-way analysis of variance (ANOVA) (if the test for normal distribution was passed) or the Kruskal-Wallis one-way ANOVA on Ranks (if the normal distribution test failed). Both were followed by a post-hoc test (Dunnett's method or Dunn's test, respectively). A $p<0.05$ was considered to be significant.

Results

Suppression of mouse ear swelling by compounds 1a and 1c after oral administration, compared to vehicle control is shown in FIG. 4A. Table 5 summarizes inhibition of the allergic contact dermatitis response by compounds 1a and 1c.

TABLE 5

Effect of orally administered compounds 1a and 1c on ear swelling in the allergic contact dermatitis response in mice.

| Compound | Inhibition of mouse ear swelling |
|---|---|
| Administration time (oral) | |
| 1a, 100 mg/kg, 1 h | 72.6*** |
| 1a, 100 mg/kg, 4 h | 73.4*** |
| 1a, 100 mg/kg, 16 h | 29.0 |
| 1c, 100 mg/kg, 1 h | 58.1** |
| 1c, 100 mg/kg, 4 h | 68.5*** |
| 1c, 100 mg/kg, 16 h | 42.7§ |
| Miltefosine, 100 mg/kg, 16 h | 47.3§ |
| Dose-response (oral) | |
| 1a, 25 mg/kg | 44.9*** |
| 1a, 100 mg/kg | 44.4*** |
| Dexamethasone, 1 mg/kg | 78.6*** |
| Dexamethasone, 3 mg/kg | 87.1*** |

**$p < 0.01$,
***$p < 0.001$ vs. vehicle control (Dunnett's post hoc test) compared to vehicle,
§$p < 0.05$ vs. vehicle control (t-test)

In the administration time study with oral administration, compounds 1a and 1c reduced ear swelling significantly (up to 73% of vehicle control) when administered 1 h or 4 h before challenge, as also shown in FIG. 4A. Miltefosine has previously been shown to be maximally effective after oral administration when given 16 h before challenge and also in this study significantly reduced ear swelling (47% of vehicle control). However, miltefosine was not as maximally effectively as compounds 1a and 1c at their optimal administration time of 4 h, reaching only 64% of the inhibitory efficacy of 1a and 69% of that of compound 1c.

In the dose-response study, compound 1a administered 4 h before challenge reduced ear swelling significantly (45%) at 25 or 100 mg/kg, as shown in FIG. 4B. In comparison, dexamethasone administered orally at doses of 1 and 3 mg/kg significantly inhibited ear swelling (78 and 87% respectively). As discussed in example 8 for the DTH response, such high doses (overdose) of dexamethasone are unsuitable for treatment of humans due to severe side effects of the corticosteroid and were used to validate the responsiveness of the model. Nevertheless, compound 1a was able to effect an inhibition equal to 52% of the highest dose of dexamethasone at doses of 1a, which showed no toxicity.

Compounds 1a (25 mg/kg and 100 mg/kg) and 1c (100 mg/kg) had a significant impact on the TDI induced inflammatory reaction. Thus, the compounds according to the invention and, in particular compound 1a and 1c, are particularly effective and thus useful for the oral pharmaceutical intervention in inflammatory diseases, in particular in atopic dermatitis.

Suppression of mouse ear swelling by compounds 1a and 1c after topical administration, compared to vehicle control is shown in FIG. 4C. Table 6 summarizes inhibition of the allergic contact dermatitis response by compounds 1a and 1c.

TABLE 6

Effect of topically administered compound 1a on ear swelling in the allergic contact dermatitis response in mice.

| Compound | Inhibition of mouse ear swelling |
|---|---|
| 1a, 2% | 67.9** |
| 1a, 6% | 63.1** |
| Diflorasone, 0.1% | 101.1*** |
| Diflorasone, 0.5% | 110.8*** |

**p < 0.01,
***p < 0.001 vs. vehicle control (Dunnett's post hoc test) compared to vehicle.
Diflorasone treatment reduced ear thickness below that of untreated mice.

Compound 1a topically administered as a solution at 2% or 6% significantly reduced ear swelling up to 68%, compared to vehicle control. The positive control, diflorasone, completely eliminated ear swelling and even reduced ear thickness to below the level of untreated mice. This indicates that the doses of diflorasone used here are not representative of a clinical benchmark, but were used to validate the responsiveness of the model. It must also be stressed, that diflorasone is one of the strongest dermal corticosteroids and is taken for severe eczema.

One of the most undesirable side-effects of corticosteroid administration is immunosuppression, which leads to the inability to effectively address parasitic infection, wound healing and tumor growth. In the current study, the local lymph node reaction after TDI challenge (lymph node weight and cell number) was determined to assess the response of immune organs. Diflorasone produced a highly significant reduction in the local lymph node reaction at both 0.1% and 0.5%, by completely inhibiting the increase in lymph node weight and cell number (FIGS. 4D and 4E), even reducing this to levels below untreated animals. In contrast, topical treatment with compound 1a at 2% or 6% did not have any impact on the local lymph node reaction (FIGS. 4D and 4E).

In view of the strong effect shown in the allergic contact dermatitis model, the compounds of the present invention and, including compound 1a, are particularly effective and thus useful for the topical pharmaceutical intervention in inflammatory diseases, in particular in atopic dermatitis. In addition, the compounds of the present invention, including compound 1a, do not show adverse effects typical of topically administered corticosteroids, such as inhibition of the lymph node reaction and loss in body weight.

Example 10: Inhibition of Collagen Type II-Induced Arthritis (CIA) in the Mouse

Introduction

The inhibitory effect of compound 1a was assessed for anti-inflammatory and anti-arthritic activity in the type II collagen-induced arthritis (CIA) model in the mouse. CIA has been proposed as a pertinent animal model of rheumatoid arthritis in humans. In this model, a peripheral arthritis is elicited by intradermal injection of homologous or heterologous (e.g. bovine, chicken) type II collagen (CII) in complete Freund's adjuvant (CFA) into rats or mice (Stuart et al., Ann Rev Immunol. 2:199-218 (1984); Marty et al., J Clin Invest. 107:631-640 (2001); Boissier et al., Eur J Immunol. 25:1184-90 (1995)). The central role played by T cells in the development of type II CIA is demonstrated by the T cell proliferative response to mouse CII in immunized mice, the successful adoptive transfer of the disease with immune cells from the spleen, and the resistance of athymic nude mice to the induction of the pathology (Stuart et al., Ann Rev Immunol. 2:199-218 (1984); Marty et al., J Clin Invest. 107:631-640 (2001)). An advantage of this model of arthritis as compared to others is the development of an arthritogenic response toward a well defined antigen (CII), which also permits the study of antigen-induced immunological phenomena and their selective modification by immunopharmacological intervention.

Materials and Methods

Materials

Bovine type II collagen (Chondrex, Redmond Wash., USA) was dissolved at 2 mg/ml in 0.05 M acetic acid by gentle stirring overnight at 4° C. CFA was prepared by adding *Mycobacterium tuberculosis* H37Ra (Difco, Detroit, Mich.)) at 2 mg/ml to IFA (incomplete Freund's adjuvant, Sigma Aldrich, Milano, Italy). Before injection, CII was emulsified with an equal volume of CFA.

Animals

Eight to 9 week old male DBA/1j mice were purchased from Harlan Laboratories srl (San Pietro al Natisone, Udine, Italy) and kept under standard laboratory conditions with free access to food and water. Mice were allowed to adapt one week to their environment before starting the study.

Induction of Collagen Induced Arthritis (CIA)

Group size was n=11 mice unless otherwise stated. Test compounds were freshly prepared before administration. Mice were injected intradermally at the base of the tail with 100 μL of an emulsion containing 100 μg of CII, IFA and 100 μg of *Mycobacterium tuberculosis*. On day 21, a boost of CII in IFA was administered.

Prophylactic Treatment

Five groups of mice were treated under a prophylactic regimen from day 0 to 47 and an additional group of sham treated mice was treated only with the CII vehicle, on days 0 and 21. Compound 1a was administered as a suspension in 0.5% carboxymethylcellulose (10 mL/kg) and, as a positive control, dexamethasone was administered at 0.3 mg/kg as detailed below:

Group 1: compound 1a at 25 mg/kg, orally by gavage, twice daily
Group 2: compound 1a at 100 mg/kg, orally by gavage, twice daily Group 3: dexamethasone 0.3 mg/kg, intraperitoneally, once daily
Group 4: vehicle (carboxymethylcellulose), orally by gavage
Group 5: sham treated mice
Animals were sacrificed on day 47 after immunization.
Therapeutic Treatment Groups of mice were treated with compound 1a from the onset of arthritic symptoms, defined as first day on which a disease score of 1 or higher was observed and mice expressing the respective disease score were randomly assigned to each experimental group. Treatment was continued for 20 consecutive days.
Group 6: compound 1a at 100 mg/kg, orally by gavage, twice daily As the treatment was based on the individual expression of arthritis symptoms, the mice were synchronized to the first day of treatment for evaluation of the disease progression. No separate vehicle group was included for the therapeutic treatment regimen hence vehicle group 4 was reanalyzed after synchronization to the first day on which a disease score of 1 or higher was observed. Animals were sacrificed after 20 days of treatment.
Clinical Assessment Mice were evaluated for arthritis daily by an observer unaware of the treatment regimens according to a macroscopic scoring system: 0=no signs of arthritis; 1=swelling and/or redness of the paw or one digit; 2=involvement of 2 joints; 3=involvement of more than 2 joints; 4=severe arthritis of the entire paw and digits. An arthritis index was calculated for each mouse by summing the scores for individual paws. Clinical severity was also determined by evaluation of paw thickness of both front and hind-paws using a thickness gauge. An index was calculated for each mouse by summing the thickness for individual paws. Body weights were also recorded daily.
Statistical Evaluation Mean and standard deviation (SD) were calculated from individual score values.

For the arthritis score two different statistical calculations were performed. For each treatment day the arthritis scores of each group were compared to the vehicle control group using the student's-t test and a $p<0.05$ was considered significant.

Additionally, a cumulative arthritis score was calculated for each treatment group by summing all arthritis scores throughout the study period. The cumulative arthritis scores were compared using the student's-t test and a $p<0.05$ was considered significant. The cumulative arthritis score requires that all animals are evaluated for the same length of time; in order to determine the cumulative arthritis score of animals which had died during the study, the missing values were substituted with the group mean for the day of the missing value. The substitution of missing values was only performed for the cumulative arthritis score and not used for other calculations.
Results
Effects of the Prophylactic Treatment of Test Compounds on Arthritic Score As expected, starting 5-6 days after the CII boost, clinical signs of arthritis became observable in vehicle treated control mice, consisting of progressively augmenting arthritic scores, accompanied by increased paw thickness. Significant loss in body weight of vehicle treated animals compared to the sham-treated group was observed after the CII boost.

Compound 1a reduced the cumulative arthritis score and paw thickness at both 25 and 100 mg/kg compared to vehicle treated mice, as shown in FIG. 5A. Dexamethasone nearly completely suppressed the clinical signs of arthritis, but also induced a significant reduction in body weight from day 8 until the end of the study, when compared to vehicle treated mice (FIG. 5B). However, no effects on body weight were observed in mice treated with compound 1a at both low and high doses (FIG. 5B).
Effects of the Therapeutic Treatment of Test Compounds on Arthritic Score Compound 1a at 100 mg/kg significantly reduced the arthritis score and the cumulative arthritis score compared to vehicle-treated mice from day 11 to 13 and on day 21, as also shown in FIG. 5C. Furthermore, a trend to a reduction in the duration of disease compared to vehicle-treated mice was observed.
Immune Organ Weights At sacrifice, thymuses and spleens were collected and weighed to assess the effect on these important immune organs. Compared to the sham-treated mice, animals treated with the vehicle exhibited a significant increase in spleen weight, due to the proliferation of lymphocytes in answer to elicitation by CII injection. As expected, treatment with the positive control drug, dexamethasone, markedly reduced the weights of both spleens and thymuses compared to both vehicle treated and sham groups demonstrating the known immunosuppressive effect of corticosteroids (FIG. 5D). In contrast, treatment with compound 1a did not reduce thymus or spleen weights compared to vehicle treated mice (FIG. 5D).

The data demonstrate that compound 1a ameliorated the clinical course of type II CIA when administered prophylactically, reducing the arthritis score and paw thickness. When administered under the therapeutic regimen, 1a a significant reduction in the cumulative disease score was evidenced. Compound 1a did not show any toxic effects, whereas dexamethasone caused a significant loss in body weight and spleen and thymus weights. These results suggest that the compounds of the present invention, including compound 1a, are particularly effective and thus useful for the medical intervention in rheumatoid arthritis.

Example 11: Pharmacokinetic Study of Five Different Batches of Compound 1a after a Single Oral Administration to Mice Introduction The aim of the study was to evaluate pharmacokinetic (PK) properties of five different batches including anydrates and monohydrates of the crystal form A of compound 1a (cf. Table 1 in Example 5) after a single oral administration to mice. Three of the forms were anhydrous and two were monohydrates.
Materials and Methods Compound 1a was administered as a suspension of 0.5% methyl cellulose (Sigma-Aldrich) in water at a dose of 100 mg/kg (10 ml/kg) by oral gavage to non-fasted female Balb/c mice (n=3). This dose had previously been shown to be well tolerated. No overt toxicity was shown regardless of the polymorphic crystal form.

Blood was collected by decapitation at 0.5, 1, 2, 4, 8, 12, 24, and 48 h after administration. Blood plasma was isolated by centrifugation at 4° C. (20,000×g for 10 min), transferred to microtubes containing lithium-heparin and frozen in aliquots at −70° C. until assayed by mass-spectrometry. Mean plasma concentration-time profiles (semi-logarithmic) of the five polymorphic crystal forms of compound 1a are shown in FIG. 6.

Pharmacokinetic Parameters

For PK evaluation, summary statistics and plotting of concentration/time curves, all values below the lower limit of quantification (LLOQ) were set to zero. PK parameters for the five forms of compound 1a are listed in Table 7.

TABLE 7

Pharmacokinetic parameters of polymorphic forms of compound 1a in female Balb/c mice (n = 3) following a single oral administration of 100 mg/kg in 0.5% methylcellulose solution.

| | Polymorphic form | | | | |
|---|---|---|---|---|---|
| PK parameter | 2338-CF/30 | 2208-CF/1 | KP-0722.11 | KP-0726.11 | TN-0382.11 |
| $c_{max}$ (ng/ml) | 1063 | 1003 | 571 | 759 | 627 |
| $t_{max}$ (h) | 1.0 | 1.0 | 2.0 | 1.0 | 1.0 |
| $c_{last}$ (ng/ml) | 1.8 | 1.1 | 3.8 | 1.2 | 3.4 |
| $t_{last}$ (h) | 48.0 | 48.0 | 24.0 | 48.0 | 24.0 |
| $AUC_{0-t}$ (ng * h/ml) | 3118 | 4400 | 3162 | 3744 | 3535 |
| $AUC_{0-inf}$ (ng * h/ml) | 3144 | 4412 | 3179 | 3758 | 3547 |
| MRT (h) | 5.5 | 5.0 | 4.8 | 5.5 | 5.9 |
| $t_{1/2}$ (h) | 9.9 | 7.3 | n.d. | 8.2 | n.d. |

$c_{max}$ Observed maximum plasma concentration
$t_{max}$ Time of occurrence of $c_{max}$
$c_{last}$ Concentration at last sampling time point
$t_{last}$ Time of last sampling time point
$AUC_{0-t}$ Area under the plasma concentration versus time curve from time zero to $t_{last}$, calculated by the trapezoidal rule
$AUC_{0-inf}$ Area under the plasma concentration versus time curve from time zero to infinity with extrapolation of the terminal phase
MRT Mean residence time calculated using trapezoid area calculations extrapolated to infinity
$t_{1/2}$ Terminal half-life The PK behaviour was comparable for all polymorphic forms of compound 1a. The compound was rapidly absorbed from the gastro-intestinal (GI)-tract, reaching a maximum plasma concentration after 1-2 h. The overall exposure was highest with form 2208-CF/1. A second plasma peak was observed at 8 h after administration of forms KP-0726.11 and TN-0382.11, indicating a second absorption window that might be caused by improved solubility of these polymorphs in the lower part of the GI-tract. The mean residence time was in the same range for all polymorphic forms tested and the PK curves and terminal half-lives were similar between 8-24 h, as also shown in FIG. 6. No terminal half-lives were determined for KP-0722.11 or TN-0382.11, due to the lack of 48 h values for these forms.

The invention claimed is:

1. A compound of the following formula 1a:

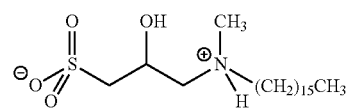

or a pharmaceutically acceptable salt or solvate thereof.

2. A pharmaceutical composition comprising the compound of claim 1 and a pharmaceutically acceptable excipient.

* * * * *

UNITED STATES PATENT AND TRADEMARK OFFICE
CERTIFICATE OF CORRECTION

| | |
|---|---|
| PATENT NO. | : 9,751,834 B2 |
| APPLICATION NO. | : 14/403168 |
| DATED | : September 5, 2017 |
| INVENTOR(S) | : Georg Schlechtingen et al. |

It is certified that error appears in the above-identified patent and that said Letters Patent is hereby corrected as shown below:

In the Specification

In Column 2 at Line 57, Change "aenes" to --genes--.

In Column 3 at Line 47, Change "Aggregation" to --aggregation--.

In Column 4 at Line 29 (approx.), Change "rhinitic," to --rhinitis,--.

In Column 4 at Line 64, Change "—$SO_3$—," to -- —$SO_3^-$—,--.

In Column 4 at Line 64, Change "—$PO_3H$—," to -- —$PO_3H^-$—,--.

In Column 5 at Line 10, Change "vennus" to --venous--.

In Column 7 at Line 51, Change "the the" to --the--.

In Column 8 at Line 21, Change "ranae" to --range--.

In Column 8 at Line 38, Change "Sury" to --Surv--.

In Column 10 at Line 17, After "—OH," insert -- —$O(C_{1-3}$ alkyl),--.

In Column 10 at Line 62, Change "—$(OH_2)p$—" to -- —$(CH_2)p$— --.

In Column 11 at Line 2, Change "—$O(OH_2)_3OH$," to -- —$O(CH_2)_3OH$,--.

In Column 11 at Line 30 (approx.), Change "—$PO_3H$—," to -- —$PO_3H^-$—,--.

In Column 13 at Line 42, Change "—$O(OH_2)_2OH$," to -- —$O(CH_2)_2OH$,--.

Signed and Sealed this
Twentieth Day of February, 2018

Andrei Iancu
*Director of the United States Patent and Trademark Office*

In Column 13 at Lines 59-60, Change "—OH$_2$—CH(—R$^{41}$)—CH$_2$—," to -- —CH$_2$—CH(—R$^{41}$)—CH$_2$—,--.

In Column 14 at Line 1, Change "—CH$_2$—CH(—OH)—OH$_2$—" to -- —CH$_2$—CH(—OH)—CH$_2$— --.

In Column 14 at Lines 1-2, Change "—CH$_2$—CH(—O—C(O)—(C$_{1-3}$ alkyl))—OH$_2$—." to -- —CH$_2$—CH(—O—C(O)—(C$_{1-3}$ alkyl))—CH$_2$—.--.

In Column 14 at Line 25 (approx.), Change "—(OH$_2$)$_p$—CH(—R$^{41}$)—CH$_2$—," to -- —(CH$_2$)$_p$—CH(—R$^{41}$)—CH$_2$—,--.

In Column 14 at Lines 46-47, Change "—CH$_2$—CH(—O—C(O)—(C$_{1-3}$ alkyl))—OH$_2$—." to -- —CH$_2$—CH(—O—C(O)—(C$_{1-3}$ alkyl))—CH$_2$—.--.

In Column 16 at Line 4, Change "—O(OH$_2$)$_3$OH," to -- —O(CH$_2$)$_3$OH,--.

In Column 17 at Line 58, Change "lymphovytic" to --lymphocytic--.

In Column 18 at Lines 1-2, Change "hypthalamic" to --hypothalamic--.

In Column 18 at Line 5, Change "Waldenstrom's" to --Waldenström's--.

In Column 18 at Line 19, Change "Szary" to --Sézary--.

In Column 20 at Line 18 (approx.), Change "—(OH$_2$)$_p$—CH(—R$^{41}$)—CH$_2$—" to -- —(CH$_2$)$_p$—CH(—R$^{41}$)—CH$_2$— --.

In Column 22 at Line 9 (approx.), Change "—CH$_2$—OH(—OH)—CH$_2$—" to -- —CH$_2$—CH(—OH)—CH$_2$— --.

In Column 22 at Line 51, Change "quarternary" to --quaternary--.

In Column 22 at Line 57, Change "w-chloro" to --ω-chloro--.

In Column 26 at Line 19, Change "suaar" to --sugar--.

In Column 27 at Line 67, Change "odulimomab," to --adalimumab,--.

In Column 29 at Line 56, Change "melagonaster" to --melanogaster--.

In Column 30 at Line 16 (approx.), Change "8-hexosaminidase" to --β-hexosaminidase--.

In Column 31 at Lines 31-32, Change "methyitetradecylamine" to --methyltetradecylamine--.

In Column 34 at Line 28 (approx.), Change "is" to --1a--.

CERTIFICATE OF CORRECTION (continued)
U.S. Pat. No. 9,751,834 B2

In Column 36 at Line 31, Change "Tyrodeis" to --Tyrode's--.

In Column 37 at Line 57 (approx.), Change "100×(test compound×negative" to --100×(test compound-negative--.

In Column 37 at Line 66 (approx.), Change "100×(1(test" to --100×(1-(test--.

In Column 39 at Line 24, Change "Buhler)." to --Bühler).--.

In Column 41 at Line 4, Change "ovaibumin," to --ovalbumin,--.

In Column 41 at Line 5, Change "mg/mi." to --mg/ml.--.

In Column 42 at Line 64, Change "(TOD," to --(TDI),--.

In Column 42 at Line 67, After "Eur" insert --J--.

In Column 43 at Line 8 (approx.), Change "(Zllner" to --(Zöllner--.

In Column 43 at Line 20, Change "Diss," to --Riss,--.

In Column 43 at Line 58, After "0.5" insert --%--.

In Column 43 at Line 59, Change "tyiose" to --tylose--.